US010919956B2

(12) United States Patent
Pier et al.

(10) Patent No.: US 10,919,956 B2
(45) Date of Patent: Feb. 16, 2021

(54) POLYSACCHARIDE VACCINE FOR STAPHYLOCOCCAL INFECTIONS

(75) Inventors: Gerald B. Pier, Brookline, MA (US); Tomas Maira-Litran, Brookline, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 1413 days.

(21) Appl. No.: 10/713,790

(22) Filed: Nov. 12, 2003

(65) Prior Publication Data

US 2005/0118198 A1  Jun. 2, 2005

Related U.S. Application Data

(60) Provisional application No. 60/425,425, filed on Nov. 12, 2002.

(51) Int. Cl.
| | | |
|---|---|---|
| C07K 16/12 | (2006.01) | |
| A61K 39/085 | (2006.01) | |
| A61K 31/715 | (2006.01) | |
| A61K 39/00 | (2006.01) | |
| C08B 37/00 | (2006.01) | |
| A61K 47/64 | (2017.01) | |

(52) U.S. Cl.
CPC ........ *C07K 16/1271* (2013.01); *A61K 31/715* (2013.01); *A61K 39/085* (2013.01); *A61K 47/646* (2017.08); *C08B 37/0063* (2013.01); *A61K 39/00* (2013.01); *A61K 2039/6037* (2013.01); *A61K 2039/6087* (2013.01); *A61K 2039/627* (2013.01); *G01N 2400/10* (2013.01)

(58) Field of Classification Search
USPC .......... 424/243.1, 184.1, 831, 234.1; 514/23, 514/54; 536/123.1, 53
See application file for complete search history.

(56) References Cited

U.S. PATENT DOCUMENTS

| | | |
|---|---|---|
| 2,842,049 A * | 7/1958 | Delangre .................. 430/199 |
| 4,197,290 A | 4/1980 | Yoshida |
| 4,285,936 A | 8/1981 | Pier et al. |
| 4,379,145 A * | 4/1983 | Masuho et al. ........... 530/391.9 |
| 4,443,549 A | 4/1984 | Sadowski |
| 4,465,776 A | 8/1984 | Pier et al. |
| 4,578,458 A | 3/1986 | Pier |
| 4,652,448 A | 3/1987 | Sadowski |
| 4,755,381 A | 7/1988 | Cryz |
| 4,786,592 A | 11/1988 | Deal et al. |
| 4,789,735 A | 12/1988 | Frank et al. |
| 4,795,803 A | 1/1989 | Lindberg et al. |
| 4,830,852 A | 5/1989 | Marburg et al. |
| 4,859,449 A | 8/1989 | Mattes |
| 4,879,272 A | 11/1989 | Shimoda et al. |
| 4,902,616 A | 2/1990 | Fournier et al. |
| 5,055,455 A | 10/1991 | Pier |
| 5,352,670 A | 10/1994 | Venot et al. |
| 5,362,754 A | 11/1994 | Raad et al. |
| 5,366,505 A | 11/1994 | Farber |
| 5,425,946 A | 6/1995 | Tai et al. |
| 5,571,511 A | 11/1996 | Fischer |
| 5,589,591 A | 12/1996 | Lewis |
| 5,688,516 A | 11/1997 | Raad et al. |
| 5,718,694 A | 2/1998 | Rupp |
| 5,763,191 A | 6/1998 | Knoll et al. |
| 5,830,539 A | 11/1998 | Yan et al. |
| 5,844,093 A | 12/1998 | Kettleborough et al. |
| 5,858,350 A | 1/1999 | Vournakis et al. |
| 5,866,140 A | 2/1999 | Fattom et al. |
| 5,872,215 A | 2/1999 | Osbourn et al. |
| 5,980,910 A | 11/1999 | Pier |
| 5,989,542 A | 11/1999 | Pier et al. |
| 6,235,883 B1 | 5/2001 | Jakobovits et al. |
| 6,245,735 B1 | 6/2001 | Pier |
| 6,399,066 B1 | 6/2002 | Pier |
| 6,743,431 B2 | 6/2004 | Pier |
| 6,822,072 B1 | 11/2004 | Edwards et al. |
| 6,903,194 B1 | 6/2005 | Sato et al. |
| 6,924,360 B2 | 8/2005 | Green et al. |
| 7,015,007 B2 | 3/2006 | Pier |
| 7,157,443 B2 * | 1/2007 | Joyce et al. ............ 514/54 |
| 7,252,828 B2 | 8/2007 | Pier et al. |
| 7,550,569 B2 | 6/2009 | Baker et al. |
| 7,723,087 B2 | 5/2010 | Pier et al. |
| 7,786,255 B2 | 8/2010 | Pier et al. |
| 8,084,595 B2 | 12/2011 | Pier et al. |
| 8,252,894 B2 | 8/2012 | Pier et al. |
| 8,350,017 B2 | 1/2013 | Pier et al. |
| 8,410,249 B2 | 4/2013 | Pier et al. |
| 8,435,515 B2 | 5/2013 | Pier et al. |

(Continued)

FOREIGN PATENT DOCUMENTS

| | | |
|---|---|---|
| CA | 2480052 A1 | 10/2003 |
| CA | 2475736 A1 | 1/2006 |

(Continued)

OTHER PUBLICATIONS

Joyce et al. Carbohydr. Res. 338: 903-922, 2003.*

(Continued)

*Primary Examiner* — Sarvamangala Devi
(74) *Attorney, Agent, or Firm* — Wolf, Greenfield & Sacks, P.C.

(57) ABSTRACT

The invention relates to compositions of a deacetylated poly N-acetylated glucosamine (dPNAG) of Staphylococci. The dPNAG may be isolated from natural sources or synthesized de novo. The invention also relates to the use of dPNAG as a vaccine for inducing active immunity to infections caused by *Staphylococcus aureus*, *S. epidermidis*, other related coagulase-negative or coagulase-positive Staphylococci, and other organisms carrying the ica (intracellular adhesion) locus. The invention further provides methods of use for antibodies directed to dPNAG, particularly for inducing passive immunity to the same class of infections.

26 Claims, 5 Drawing Sheets

Specification includes a Sequence Listing.

(56) References Cited

U.S. PATENT DOCUMENTS

| | | | |
|---|---|---|---|
| 8,454,979 B2* | 6/2013 | Mitarai | A61K 35/74 424/282.1 |
| 8,461,319 B2 | 6/2013 | Pier et al. | |
| 8,492,364 B2 | 7/2013 | Pier et al. | |
| 8,663,654 B2 | 3/2014 | Pier et al. | |
| 8,703,148 B2* | 4/2014 | Biemans et al. | 424/194.1 |
| 8,912,314 B2 | 12/2014 | Pier et al. | |
| 8,933,218 B2 | 1/2015 | Biemans et al. | |
| 9,458,227 B2 | 10/2016 | Pier et al. | |
| 9,474,806 B2 | 10/2016 | Pier et al. | |
| 10,017,563 B2 | 7/2018 | Pier et al. | |
| 10,034,927 B2 | 7/2018 | Pier et al. | |
| 2001/0048929 A1 | 12/2001 | Chong et al. | |
| 2002/0031528 A1 | 3/2002 | Fattom | |
| 2002/0119166 A1 | 8/2002 | Pier et al. | |
| 2003/0003100 A1 | 1/2003 | Levy et al. | |
| 2003/0113350 A1 | 6/2003 | Fattom et al. | |
| 2003/0124631 A1 | 7/2003 | Pier et al. | |
| 2004/0005632 A1 | 1/2004 | Erlanson et al. | |
| 2004/0018198 A1 | 1/2004 | Gudas et al. | |
| 2004/0091494 A1 | 5/2004 | Pier et al. | |
| 2004/0175731 A1 | 9/2004 | Pier et al. | |
| 2005/0025775 A1 | 2/2005 | Pier et al. | |
| 2006/0115486 A1 | 6/2006 | Pier et al. | |
| 2009/0162341 A1 | 6/2009 | Foster et al. | |
| 2010/0021503 A1 | 1/2010 | Denoel et al. | |
| 2010/0303852 A1 | 12/2010 | Biemans et al. | |
| 2010/0322959 A1 | 12/2010 | Biemans et al. | |
| 2011/0008385 A1 | 1/2011 | Castado et al. | |
| 2011/0150880 A1 | 6/2011 | Pier et al. | |
| 2012/0189700 A1 | 7/2012 | Aguilar | |
| 2014/0037633 A1 | 2/2014 | Pier et al. | |
| 2014/0206016 A1 | 7/2014 | Lozano Sanchez | |
| 2015/0165016 A1* | 6/2015 | Pier | A61K 31/715 424/137.1 |
| 2016/0375117 A1 | 12/2016 | Pier et al. | |
| 2017/0226194 A1 | 8/2017 | Pier et al. | |
| 2019/0117754 A1 | 4/2019 | Pier et al. | |
| 2019/0127448 A1 | 5/2019 | Pier et al. | |

FOREIGN PATENT DOCUMENTS

| | | | |
|---|---|---|---|
| CN | 1252807 | | 5/2000 |
| CN | 01136484 | | 4/2002 |
| CN | 1344722 | A * | 4/2002 |
| CN | 101001874 | | 7/2007 |
| CN | 100351260 | C | 11/2007 |
| DE | 69113102 | T2 | 3/1996 |
| EP | 0 302 781 | A1 | 2/1989 |
| EP | 0 574 000 | A1 | 12/1993 |
| EP | 0 694 309 | A2 | 10/1996 |
| EP | 2 315 747 | A2 | 5/2011 |
| FR | 2 410 043 | A1 | 6/1979 |
| FR | 2 581 877 | A1 | 11/1986 |
| FR | 2 640 628 | A1 | 12/1988 |
| GB | 2 009 771 | A | 6/1979 |
| JP | H02-22234 | | 1/1990 |
| JP | H11-509861 | A | 8/1999 |
| JP | H11-322793 | A | 11/1999 |
| JP | 2001-500528 | A | 1/2001 |
| JP | 2002-503705 | A | 2/2002 |
| JP | 2002-520374 | A | 7/2002 |
| JP | 2005-515237 | A | 5/2005 |
| JP | 2006-513166 | | 4/2006 |
| KR | 10-2005-0074582 | | 7/2005 |
| WO | WO 85/05037 | A1 | 11/1985 |
| WO | WO 86/02358 | A1 | 4/1986 |
| WO | WO 88/02028 | A1 | 3/1988 |
| WO | WO 89/04873 | A1 | 6/1989 |
| WO | WO 90/03398 | A1 | 4/1990 |
| WO | WO 90/06696 | A2 | 6/1990 |
| WO | WO 93/01276 | A1 | 1/1993 |
| WO | WO 93/09811 | A1 | 5/1993 |
| WO | WO 93/19373 | A1 | 9/1993 |
| WO | WO 94/15640 | A1 | 7/1994 |
| WO | WO 97/17334 | A1 | 5/1997 |
| WO | WO 97/19105 | A1 | 5/1997 |
| WO | WO 98/47915 | A1 | 10/1998 |
| WO | WO 98/52605 | A1 | 11/1998 |
| WO | WO 99/40440 | A1 | 8/1999 |
| WO | WO 99/42130 | A1 | 8/1999 |
| WO | WO 00/03745 | A2 | 1/2000 |
| WO | WO 00/35504 | A1 | 6/2000 |
| WO | WO 2000/056360 | A2 | 9/2000 |
| WO | WO 2002/094983 | A2 | 11/2002 |
| WO | WO 03/053462 | A2 | 7/2003 |
| WO | WO 2003/061558 | A2 | 7/2003 |
| WO | WO 03/085093 | A2 | 10/2003 |
| WO | WO 2003/080672 | A1 | 10/2003 |
| WO | WO 2003/087054 | A2 | 10/2003 |
| WO | WO 2004/043405 | A2 | 5/2004 |
| WO | WO 2004/080490 | A2 | 9/2004 |
| WO | WO 2004/043407 | A2 | 10/2004 |
| WO | WO 2005/000346 | A1 | 1/2005 |
| WO | WO 2005/016973 | A1 | 2/2005 |
| WO | WO 2005/103084 | | 11/2005 |
| WO | WO 2006/032472 | A2 | 3/2006 |
| WO | WO 2006/065503 | A2 | 6/2006 |
| WO | WO 2006/065553 | A2 | 6/2006 |
| WO | WO 2006/096970 | A1 | 9/2006 |
| WO | WO 2007/113223 | A2 | 10/2007 |
| WO | WO 2007/113224 | A2 | 10/2007 |
| WO | WO 2010/011284 | A2 | 1/2010 |

OTHER PUBLICATIONS

Maira-Litran et al. Infect. Immune. 73: 6752-6762, 2005.*
Fattom et al. Infect. Immun. 66: 4588-4592, 1998.*
Wessels et al. Infect. Immun. 66: 2186-2192, 1998.*
Maira-Litran et al. In: Abstracts of the General Meeting of the American Society for Microbiology, Orlando, Florida, pp. 283-284, #D-42, May 20-24, 2001.*
Maira-Litran et al. Infect. Immun. 73: 6752-6762, Oct. 200.*
Du Yuguo English abstract of Chinese patent application 0113648, published 417/02.*
Defaye et al. English abstract of FR 2,640,628.*
Yang et al. Tetrahedron Lett. 43: 7561-7563, Oct. 2002.*
Gening et al. Infect. Immun. 78: 764-772, 2009.*
Gotz. Mol. Microbiol. 43: 1367-1378, Mar. 2002.*
Du Yuguo. English Translation of CN 1344722. Apr. 17, 2002.*
Rohde et al. Eur. J. Cell Biol. 89: 103-111, 2010.*
Pozzi et al. PLoS One 10: e46648, Oct. 15, 2012.*
Sadovskaya et al. Clin. Vaccine Immunol. 14: 1609-1615, 2007.*
Hinnebusch et al. Curr. Top. Microbiol. Immunol. 322: 229-248, 2008.*
Chibba et al. (Org. Biomol. Chem. 10: 7103-7107, 2012.*
Genbank Submission; NIH/NCBI, Accession No. BA000018; Kuroda et al.; Oct. 22, 2004 (last submission).
Ammendolia et al., Slime production and expression of the slime-associated antigen by staphylococcal clinical isolates. J Clin Microbiol. Oct. 1999;37(10):3235-8.
Barsham et al., Detection of antibodies to *Staphylococcus epidermidis* in infected total hip replacements by an enzyme linked immunosorbent assay. J Clin Pathol. Jul. 1985;38(7):839-40.
Bernstein, et al., Antibody coated bacteria in otitis media with effusions. Ann Otol Rhinol Laryngol Suppl. May-Jun. 1980;89(3 Pt 2):104-9. Abstract only.
Capek et al., Chapters 22: Carbohydrates and Chapter 23: Polysaccharides. in Journal of Chromatography Journal Library—vol. 3: Liquid Column Chromatography, A Survey of Modem Technicques and Applications. Deyl et al., eds. Elsevier Scientific Publishing Company: New York, 1975. p. 465-528.
Chanter, Partial purification and characterization of two non K99 mannose-resistant haemagglutinins of *Escherichia coli* B41. J Gen Microbiol. Jan. 1983;129(1):235-43.
Chen et al., Characterization and biological properties of chemically deglycosylated human chorionic gonadotropin. Role of carbohydrate moieties in adenylate cyclase activation. J Biol Chem. Dec. 10, 1982;257(23):14446-52.

(56) References Cited

OTHER PUBLICATIONS

Christensen et al., Adherence of slime-producing strains of *Staphylococcus epidermidis* to smooth surfaces. Infect Immun. Jul. 1982;37(1):318-26.
Chu et al., Preparation, characterization, and immunogenicity of conjugates composed of the O-specific polysaccharide of Shigella dysenteriae type 1 (Shiga's bacillus) bound to tetanus toxoid. Infect Immun. Dec. 1991;59(12):4450-8.
Conlon et al., icaR encodes a transcriptional repressor involved in environmental regulation of ica operon expression and biofilm formation in *Staphylococcus epidermidis*. J Bacteriol. Aug. 2002;184(16):4400-8.
Conlon et al., Regulation of icaR gene expression in *Staphylococcus epidermidis*. FEMS Microbiol Lett. Nov. 5, 2002;216(2):171-7.
Cramton et al., The intercellular adhesion (ica) locus is present in *Staphylococcus aureus* and is required for biofilm formation. Infect Immun. Oct. 1999;67(10):5427-33.
Dobrin, et al., The role of complement, immunoglobulin and bacterial antigen in coagulase-negative staphylococcal shunt nephritis. Am J Med. Nov. 1975;59(5):660-73. Abstract only.
Elder et al., Characterization of monoclonal antibodies specific for adhesion: isolation of an adhesin of *Streptococcus sanguis* FW213. Infect Immun. Nov. 1986;54(2):421-7.
Espersen, et al., Solid-phase radioimmunoassay for IgG antibodies to *Staphylococcus epidermidis*. Use in serious coagulase-negative staphylococcal infections. Arch Intern Med. Apr. 1987;147(4):689-93. Abstract only.
Espersen, et al., Enzyme-linked immunosorbent assay for detection of *Staphylococcus epidermidis* antibody in experimental *S. epidermidis* endocarditis. J Clin Microbiol. Feb. 1986;23(2):339-42.
Fattom et al., Synthesis and immunologic properties in mice of vaccines composed of *Staphylococcus aureus* type 5 and type 8 capsular polysaccharides conjugated to Pseudomonas aeruginosa exotoxin A. Infect Immun. Jul. 1990;58(7):2367-74.
Fattom et al., Effect of conjugation methodology, carrier protein, and adjuvants on the immune response to *Staphylococcus aureus* capsular polysaccharides. Vaccine. Oct. 1995;13(14):1288-93.
Ferreiros et al., Purification and partial characterization of a K99-antigen associated adhesin in *Escherichia coli* (637 strain). Rev Esp Fisiol. Mar. 1983;39(1):45-50.
Fournier et al., Purification and characterization of *Staphylococcus aureus* type 8 capsular polysaccharide. Infect Immun. Jul. 1984;45(1):87-93.
Gerke et al., Characterization of the N-acetylglucosaminyltransferase activity involved in the biosynthesis of the *Staphylococcus epidermidis* polysaccharide intercellular adhesin. J Biol Chem. Jul. 17, 1998;273(29):18586-93.
Gray et al., Effect of extracellular slime substance from *Staphylococcus epidermidis* on the human cellular immune response. Lancet. Feb. 18, 1984;1(8373):365-7.
Heilmann et al., Molecular basis of intercellular adhesion in the biofilm-forming *Staphylococcus epidermidis*. Mol Microbiol. Jun. 1996;20(5):1083-91.
Heilmann et al., Characterization of Tn917 insertion mutants of *Staphylococcus epidermidis* affected in biofilm formation. Infect Immun. Jan. 1996;64(1):277-82.
Hogt et al., Cell surface characteristics of coagulase-negative staphylococci and their adherence to fluorinated poly(ethylenepropylene). Infect Immun. Jan. 1986;51(1):294-301.
Ichiman et al., The relationship of capsular-type of *Staphylococcus epidermidis* to virulence and induction of resistance in the mouse. J Appl Bacteriol. Oct. 1981;51(2):229-41.
Ichiman et al., Induction of resistance with heat-killed unencapsulated strains of *Staphylococcus epidermidis* against challenge with encapsulated strains of *Staphylococcus epidermidis*. Microbiol Immunol. 1989;33(4):277-86.
Ichiman et al., Relation of human serum antibody against *Staphylococcus epidermidis* cell surface polysaccharide detected by enzyme-linked immunosorbent assay to passive protection in the mouse. J Appl Bacteriol. Aug. 1991;71(2):176-81.
Ichiman et al., Specificity of monoclonal antibodies against an encapsulated strain of *Staphylococcus epidermidis*. in The Staphylococci, Zbl Bakt. 1991;Suppl 21:150-2.
Jefferson et al., Identification of a 5-nucleotide sequence that controls expression of the ica locus in *Staphylococcus aureus* and characterization of the DNA-binding properties of IcaR. Mol Microbiol. May 2003;48(4):889-99.
Jefferson et al., The teicoplanin-associated locus regulator (TcaR) and the intercellular adhesin locus regulator (IcaR) are transcriptional inhibitors of the ica locus in *Staphylococcus aureus*. J Bacteriol. Apr. 2004;186(8):2449-56.
Johnson et al., Interference with granulocyte function by *Staphylococcus epidermidis* slime. Infect Immun. Oct. 1986;54(1):13-20.
Kelly-Quintos et al., Biological Characterization of Fully Human Monoclonal Antibodies to Staphylococcal Surface Polysaccharide PNAG. Abstracts of the 104th General Meeting of the American Society for Microbiology. Am Soc Microbiol. May 2004;abstract A-63. Abstract and corresponding presentation.
Keutmann et al., Evidence for a conformational change in deglycosylated glycoprotein hormones. FEBS Lett. Jun. 17, 1985;185(2):333-8.
Kohler, Derivation and diversification of monoclonal antibodies. Science. Sep. 19, 1986;233(4770):1281-6.
Kojima et al., Antibody to the capsular polysaccharide/adhesin protects rabbits against catheter-related bacteremia due to coagulase-negative staphylococci. J Infect Dis. Aug. 1990; 162(2):435-41.
Kuroda et al., Whole genome sequencing of meticillin-resistant *Staphylococcus aureus*. Lancet. Apr. 21, 2001;357(9264):1225-40.
Lee et al., Chemical characterization and immunogenicity of capsular polysaccharide isolated from mucoid *Staphylococcus aureus*. Infect Immun. Sep. 1987;55(9):2191-7.
Lee et al., Protective efficacy of antibodies to the *Staphylococcus aureus* type 5 capsular polysaccharide in a modified model of endocarditis in rats. Infect Immun. Oct. 1997;65(10):4146-51.
Leith et al., Purification of a Mycoplasma pneumoniae adhesin by monoclonal antibody affinity chromatography. J Bacteriol. Feb. 1984;157(2):678-80.
Locksley, Chapter 94: Staphylococcal Infections. In Harrison's Principles of Internal Medicine, Eleventh Edition. Braunwald et al., eds. McGraw-Hill Book Company, Inc.: New York, 1950. p. 537-543.
Ludwicka et al., Investigation on extracellular slime substance produced by *Staphylococcus epidermidis*. Zentralbl Bakteriol Mikrobiol Hyg [A]. Dec. 1984;258(2-3):256-67.
Mack et al., Association of biofilm production of coagulase-negative staphylococci with expression of a specific polysaccharide intercellular adhesin. J Infect Dis. Oct. 1996;174(4):881-4.
Mack et al., Characterization of transposon mutants of biofilm-producing *Staphylococcus epidermidis* impaired in the accumulative phase of biofilm production: genetic identification of a hexosamine-containing polysaccharide intercellular adhesin. Infect Immun. Aug. 1994;62(8):3244-53.
Mack et al., Parallel induction by glucose of adherence and a polysaccharide antigen specific for plastic-adherent *Staphylococcus epidermidis*: evidence for functional relation to intercellular adhesion. Infect Immun. May 1992;60(5):2048-57.
Mack et al., Essential functional role of the polysaccharide intercellular adhesin of *Staphylococcus epidermidis* in hemagglutination. Infect Immun. Feb. 1999;67(2):1004-8.
Mack et al., Identification of three essential regulatory gene loci governing expression of *Staphylococcus epidermidis* polysaccharide intercellular adhesin and biofilm formation. Infect Immun. Jul. 2000;68(7):3799-807.
Maira-Litran et al., Deacetylated-poly-N-acetyl Glucosamine (dPNAG) Polysaccharide Conjugated to Diphtheria Toxoid (DT) Confers Protection Against Multiple Strains of *Staphylococcus aureus* in a Murine Model of Bacteremia. Abstracts of the 104th General Meeting of the American Society for Microbiology. Am Soc Microbiol. May 2004;abstract D-130. Abstract and corresponding presentation.
Maira-Litran et al., Synthesis and Immunological Properties of a Staphylococcal Deacetylated-poly-N-acetyl Glucosamine (dPNAG) Polysaccharide and Clumping Factor A (ClfA) Protein Conjugate Vaccine. Abstracts of the 104th General Meeting of the American

(56) References Cited

OTHER PUBLICATIONS

Society for Microbiology. Am Soc Microbiol. May 2004;abstract E-062. Abstract and corresponding presentation.
McKenney et al., Broadly protective vaccine for *Staphylococcus aureus* based on an in vivo-expressed antigen. Science. May 28, 1999;284(5419):1523-7.
McKenney et al., Vaccine potential of poly-1-6 beta-D-N-succinylglucosamine, an immunoprotective surface polysaccharide of *Staphylococcus aureus* and *Staphylococcus epidermidis*. J Biotechnol. Sep. 29, 2000;83(1-2):37-44.
Melean et al., Toward the automated solid-phase synthesis of oligoglucosamines: systematic evaluation of glycosyl phosphate and glycosyl trichloroacetimidate building blocks. Carbohydr Res. Nov. 19, 2002;337(21-23):1893-916.
Milstein, From antibody structure to immunological diversification of immune response. Science. Mar. 14, 1986;231(4743):1261-8.
Moch et al., Isolation and characterization of the alpha-sialyl-beta-2,3-galactosyl-specific adhesin from fimbriated *Escherichia coli*. Proc Natl Acad Sci U S A. May 1987;84(10):3462-6.
Moreau et al., Structure of the type 5 capsular polysaccharide of *Staphylococcus aureus*. Carbohydr Res. Jul. 1, 1990;201(2):285-97.
Muller et al., Occurrence of capsular polysaccharide/adhesin among clinical isolates of coagulase-negative staphylococci. J Infect Dis. Nov. 1993;168(5):1211-8.
Nagy et al., Multi-adhesin vaccines for the protection of the neonatal piglet against "*E. coli*" infections. Dev Biol Stand. 1983;53:189-97.
Nakano, et al., Polyclonal antibody production in murine spleen cells induced by *Staphylococcus*. Microbiol Immunol. 1980;24(10):981-94. Abstract only.
Ohshima et al., Cell surface antigen of encapsulated *Staphylococcus epidermidis* ATCC 31432. J Clin Microbiol. Jul. 1987;25(7):1338-40.
Ohshima et al., Protection inducing antigen of an encapsulated *Staphylococcus epidermis* SE-10. in The Staphylococci, Zbl Bakt. 1991;Suppl 21:279-80.
Orskov et al., An adhesive protein capsule of *Escherichia coli*. Infect Immun. Jan. 1985;47(1):191-200.
Peters et al., Biology of s.epidermidis extracellular slime. in The Staphylococci, Zbl Bakt. 1987;Suppl 16:15-33.
Quie et al., Coagulase-negative staphylococcal adherence and persistence. J Infect Dis. Oct. 1987; 156(4):543-7.
Rogemond et al., Lectinlike adhesins in the Bacteroides fragilis group. Infect Immun. Jul. 1986;53(1):99-102.
Rupp et al., Characterization of the importance of polysaccharide intercellular adhesin/hemagglutinin of *Staphylococcus epidermidis* in the pathogenesis of biomaterial-based infection in a mouse foreign body infection model. Infect Immun. May 1999;67(5):2627-32.
Rupp et al., Characterization of *Staphylococcus epidermidis* polysaccharide intercellular adhesin/hemagglutinin in the pathogenesis of intravascular catheter-associated infection in a rat model. Infect Immun. May 1999;67(5):2656-9.
Sanford et al., Detection of staphylococcal membrane receptors on virus-infected cells by direct adhesin overlay. Infect Immun. Jun. 1986;52(3):671-5.
Schumacher-Perdreau et al., Comparative analysis of a biofilm-forming *Staphylococcus epidermidis* strain and its adhesion-positive, accumulation-negative mutant M7. FEMS Microbiol Lett. Mar. 15, 1994;117(1):71-8.
Sompolinsky et al., Encapsulation and capsular types in isolates of *Staphylococcus aureus* from different sources and relationship to phage types. J Clin Microbiol. Nov. 1985;22(5):828-34.
Takeda et al., Protection against endocarditis due to *Staphylococcus epidermidis* by immunization with capsular polysaccharide/adhesin. Circulation. Dec. 1991;84(6):2539-46.
Thomas et al., Enzyme-linked lectinsorbent assay measures N-acetyl-D-glucosamine in matrix of biofilm produced by *Staphylococcus epidermidis*. Curr Microbiol. Oct. 1997;35(4):249-54.
Tojo et al., Isolation and characterization of a capsular polysaccharide adhesin from *Staphylococcus epidermidis*. J Infect Dis. Apr. 1988;157(4):713-22.
Tollersrud et al., Genetic and serologic evaluation of capsule production by bovine mammary isolates of *Staphylococcus aureus* and other *Staphylococcus* spp. from Europe and the United States. J Clin Microbiol. Aug. 2000;38(8):2998-3003.
Vershigora et al., Secretory antibodies to homologous and heterologous staphylococcal strains in the colostrum of rabbits. Zh Mikrobiol Epidemiol Immunobiol. 1980;88-90. Russian.
Vuong et al., A crucial role for exopolysaccharide modification in bacterial biofilm formation, immune evasion, and virulence. J Biol Chem. Dec. 24, 2004;279(52):54881-6. Epub Oct. 22, 2004.
Wang et al., The pgaABCD locus of *Escherichia coli* promotes the synthesis of a polysaccharide adhesin required for biofilm formation. J Bacteriol. May 2004;186(9):2724-34.
Wessels et al., Isolation and characterization of type IV group B *Streptococcus* capsular polysaccharide. Infect Immun. Apr. 1989;57(4):1089-94.
Wray et al., Identification and characterization of a uroepithelial cell adhesin from a uropathogenic isolate of Proteus mirabilis. Infect Immun. Oct. 1986;54(1):43-9.
Yamada, et al., Possible common biological and immunological properties for detecting encapsulated strains of *Staphylococcus epidermidis*. J Clin Microbiol. Oct. 1988;26(10):2167-72.
Yoshida et al., Mouse virulent strain of *Staphylococcus epidermidis*. Relation of antiphagocytic activity to the protection-inducing antigen. Jpn J Microbiol. Jun. 1976;20(3):209-17.
Yoshida, et al., Immunological response to a strain of *Staphylococcus epidermidis* in the rabbit: production of protective antibody. J Med Microbiol. Nov. 1978;11(4):371-7. Abstract only.
Yoshida et al., Cross protection between a strain of *Staphylococcus epidermidis* and eight other species of coagulase-negative staphylococci. Can J Microbiol. Jul. 1988;34(7):913-5.
Youmans, Staphylococci, Staphylococcal Disease, and Toxic Shock Syndrome. in the Biologic and Clinical Basis of Infectious Diseases, Third Edition . . . Youmans et al., eds. W.B. Saunders Company: Philadelphia, 1985. p. 618-29 and 738-9.
Ziebuhr et al., Detection of the intercellular adhesion gene cluster (ica) and phase variation in *Staphylococcus epidermidis* blood culture strains and mucosal isolates. Infect Immun. Mar. 1997;65(3):890-6.
Ziebuhr et al., A novel mechanism of phase variation of virulence in *Staphylococcus epidermidis*: evidence for control of the polysaccharide intercellular adhesin synthesis by alternating insertion and excision of the insertion sequence element IS256. Mol Microbiol. Apr. 1999;32(2):345-56.
Allignet et al., Tracking adhesion factors in *Staphylococcus caprae* strains responsible for human bone infections following implantation of orthopaedic material. Microbiology. Aug. 1999;145 ( Pt 8):2033-42.
Arciola et al., In catheter infections by *Staphylococcus epidermidis* the intercellular adhesion (ica) locus is a molecular marker of the virulent slime-producing strains. J Biomed Mater Res. Mar. 5, 2002;59(3):557-62. Abstract Only.
Bhasin et al., Identification of a gene essential for O-acetylation of the *Staphylococcus aureus* type 5 capsular polysaccharide. Mol Microbiol. Jan. 1998;27(1):9-21. Abstract Only.
Cramton et al., Anaerobic conditions induce expression of polysaccharide intercellular adhesin in *Staphylococcus aureus* and *Staphylococcus epidermidis*. Infect Immun. Jun. 2001;69(6):4079-85.
Dobinsky et al., Influence of Tn917 insertion on transcription of the icaADBC operon in six biofilm-negative transposon mutants of *Staphylococcus epidermidis*. Plasmid. Jan. 2002;47(1):10-7. Abstract Only.
Fattom et al., Antigenic determinants of *Staphylococcus aureus* type 5 and type 8 capsular polysaccharide vaccines. Infect Immun. Oct. 1998;66(10):4588-92.
Fey et al., Characterization of the relationship between polysaccharide intercellular adhesin and hemagglutination in *Staphylococcus epidermidis*. J Infect Dis. Jun. 1999;179(6):1561-4. Abstract Only.
Fowler et al., The intercellular adhesin locus ica is present in clinical isolates of *Staphylococcus aureus* from bacteremic patients with

(56) References Cited

OTHER PUBLICATIONS infected and uninfected prosthetic joints. Med Microbiol Immunol (Berl). Apr. 2001;189(3):127-31. Abstract Only.
Frebourg et al., PCR-Based assay for discrimination between invasive and contaminating *Staphylococcus epidermidis* strains. J Clin Microbiol. Feb. 2000;38(2):877-80.
Gelosia et al., Phenotypic and genotypic markers of *Staphylococcus epidermidis* virulence. Clin Microbiol Infect. Apr. 2001;7(4):193-9. Abstract Only.
Heilmann et al., Further characterization of *Staphylococcus epidermidis* transposon mutants deficient in primary attachment or intercellular adhesion. Zentralbl Bakteriol. Jan. 1998;287(1-2):69-83. Abstract Only.
Ji et al., Regulated antisense RNA eliminates alpha-toxin virulence in *Staphylococcus aureus* infection. J Bacteriol. Nov. 1999;181(21):6585-90.
Ji et al., Identification of critical staphylococcal genes using conditional phenotypes generated by antisense RNA. Science. Sep. 21, 2001;293(5538):2266-9.
Kolberg et al., Monoclonal antibodies with specificities for *Streptococcus pneumoniae* group 9 capsular polysaccharides. FEMS Immunol Med Microbiol. Apr. 1998;20(4):249-55. Abstract Only.
Longworth et al., O-Acetylation status of the capsular polysaccharides of serogroup Y and W135 meningococci isolated in the UK. FEMS Immunol Med Microbiol. Jan. 14, 2002;32(2):119-23. Abstract Only.
Mack et al., Molecular mechanisms of *Staphylococcus epidermidis* biofilm formation. J Hosp Infect. Dec. 1999;43 Suppl:S113-25. Abstract Only.
Mack et al., Genetic and biochemical analysis of *Staphylococcus epidermidis* biofilm accumulation. Methods Enzymol. 2001;336:215-39.
McNeely et al., Antibody responses to capsular polysaccharide backbone and O-acetate side groups of *Streptococcus pneumoniae* type 9V in humans and rhesus macaques. Infect Immun. Aug. 1998;66(8):3705-10.
Michon et al., Structure activity studies on group C meningococcal polysaccharide-protein conjugate vaccines: effect of O-acetylation on the nature of the protective epitope. Dev Biol (Basel). 2000;103:151-60. Abstract Only.
Muller et al., Capsular polysaccharide/adhesin (PS/A) production by coagulase-negative staphylococci (CNS) is associated with adherence to silastic tubing. 1989. p. 49. Abstract B-111.
Maira-Litran et al., Immunochemical properties of the staphylococcal poly-N-acetylglucosamine surface polysaccharide. Infect Immun. Aug. 2002;70(8):4433-40.
McKenney et al., The ica locus of *Staphylococcus epidermidis* encodes production of the capsular polysaccharide/adhesin. Infect Immun. Oct. 1998;66(10):4711-20.
Mack et al., The intercellular adhesin involved in biofilm accumulation of *Staphylococcus epidermidis* is a linear beta-1,6-linked glucosaminoglycan: purification and structural analysis. J Bacteriol. Jan. 1996;178(1):175-83.
Baldassarri et al., Purification and characterization of the staphylococcal slime-associated antigen and its occurrence among *Staphylococcus epidermis* clinical isolates. Infect Immun. Aug. 1996;64(8):3410-5.
Gerke et al., Experimental Pseudomonas aeruginosa infection of the mouse cornea. Infection and Immunity. 1971;3(2):209-16.
Götz, *Staphylococcus* and biofilms. Mol Microbiol. Mar. 2002;43(6):1367-78.
Maira-Litran et al., Comparative opsonic and protective activities of *Staphylococcus aureus* conjugate vaccines containing native or deacetylated Staphylococcal Poly-N-acetyl-beta-(1-6)-glucosamine. Infect Immun. Oct. 2005;73(10):6752-62. Abstract Only.
Pier et al., Isolation and characterization of a high-molecular-weight polysaccharide from the slime of Pseudomonas aeruginosa. Infect Immun. Dec. 1978;22(3):908-18.
Pier et al., Protective immunity induced in mice by immunization with high-molecular-weight polysaccharide from Pseudomonas aeruginosa. Infect Immun. Dec. 1978;22(3):919-25.
Pier et al., Further purification and characterization of high-molecular-weight polysaccharide from Pseudomonas aeruginosa. Infect Immun. Dec. 1983;42(3):936-41.
Kelly-Quintos et al., Characterization of the opsonic and protective activity against *Staphylococcus aureus* of fully human monoclonal antibodies specific for the bacterial surface polysaccharide poly-N-acetylglucosamine. Infect Immun. May 2006;74(5):2742-50.
Kossaczka et al., Synthesis and immunological properties of Vi and di-O-acetyl pectin protein conjugates with adipic acid dihydrazide as the linker. Infect Immun. Jun. 1997;65(6):2088-93.
Ohshima et al., Immunochemical characterization and biological properties of a cell surface antigen extracted from encapsulated *Staphylococcus epidermidis* strain SE-10. Zentralbl Bakteriol 1990;274:417-25.
Excerpt from GENBANK Submission; NIH/NCBI; Accession No. BA000018 nucleotides 2770021-2771880; Kuroda et al., Oct. 22, 2004 (last submission).
EBI Dbfetch Submission; EMBL-EBI; Accession No. U43366; Heilmann et al., Apr. 17, 2005 (last submission).
Fitzpatrick et al., Environmental regulation of biofilm formation in intensive care unit isolates of *Staphylococcus epidermidis*. J Hosp Infect. Nov. 2002;52(3):212-8.
O'Gara et al., *Staphylococcus epidermidis* biofilms: importance and implications. J Med Microbiol. Jul. 2001;50(7):582-7.
GenBank Submission;NIH/BCBI; Accession No. DQ231549; Kelly-Quintos et al; Printed May 9, 2006.
GenBank Submission;NIH/BCBI; Accession No. DQ231550; Kelly-Quintos et al; Printed May 9, 2006.
GenBank Submission;NIH/BCBI; Accession No. DQ231551; Kelly-Quintos et al; Printed May 9, 2006.
GenBank Submission;NIH/BCBI; Accession No. DQ231552; Kelly-Quintos et al; Printed May 9, 2006.
GenBank Submission;NIH/BCBI; Accession No. DQ231553; Kelly-Quintos et al; Printed May 9, 2006.
GenBank Submission;NIH/BCBI; Accession No. DQ231554; Kelly-Quintos et al; Printed May 9, 2006.
GenBank Submission;NIH/BCBI; Accession No. AF086783; Cramton et al; BCT Oct. 1, 1999.
GenBank Submission;NIH/BCBI; Accession No. AAZ87998; Pier et al; May 31, 2000.
New York Times, Editorial, Another Very Scary Germ. Nov. 20, 2007. Available at http://www.nytimes.com/2007/11/20/opinion/20tue2.html?_r=2&oref=slogin&pagewanted. Last accessed Apr. 30, 2010. 2 pages.
Cerca et al., Comparative antibody-mediated phagocytosis of *Staphylococcus epidermidis* cells grown in a biofilm or in the planktonic state. Infect Immun. Aug. 2006;74(8):4849-55.
Cerca et al., Influence of batch or fed-batch growth on *Staphylococcus epidermidis* biofilm formation. Lett Appl Microbiol. 2004;39(5):420-4.
Cerca et al., Molecular basis for preferential protective efficacy of antibodies directed to the poorly acetylated form of staphylococcal poly-N-acetyl-beta-(1-6)-glucosamine. Infect Immun. Jul. 2007;75(7):3406-13. Epub Apr. 30, 2007.
Cerca et al., Protection against *Escherichia coli* infection by antibody to the *Staphylococcus aureus* poly-N-acetylglucosamine surface polysaccharide. Proc Natl Acad Sci U S A. May 1, 2007;104(18):7528-33. Epub Apr. 19, 2007.
De Pascalis et al., Grafting of "abbreviated" complementarity-determining regions containing specificity-determining residues essential for ligand contact to engineer a less immunogenic humanized monoclonal antibody. J Immunol. Sep. 15, 2002;169(6):3076-84.
Huang et al., Risk of methicillin-resistant *Staphylococcus aureus* infection after previous infection or colonization. Clin Infect Dis. Feb. 1, 2003;36(3):281-5. Epub Jan. 17, 2003.
Kelly-Quintos et al., The role of epitope specificity in the human opsonic antibody response to the staphylococcal surface polysaccharide poly N-acetyl glucosamine. J Infect Dis. Dec. 1, 2005;192(11):2012-9. Epub Nov. 1, 2005.

(56) References Cited

OTHER PUBLICATIONS

Klevens et al., Invasive methicillin-resistant *Staphylococcus aureus* infections in the United States. JAMA. Oct. 17, 2007;298(15):1763-71.

Kropec et al., Poly-N-acetylglucosamine production in *Staphylococcus aureus* is essential for virulence in murine models of systemic infection. Infect Immun. Oct. 2005;73(10):6868-76.

Kuehnert et al., Methicillin-resistant-*Staphylococcus aureus* hospitalizations, United States. Emerg Infect Dis. Jun. 2005;11(6):868-72. Erratum in: Emerg Infect Dis. Sep. 2006;12(9):1472.

Maccallum et al., Antibody-antigen interactions: contact analysis and binding site topography. J Mol Biol. Oct. 11, 1996;262(5):732-45.

Maira-Litran et al., Biologic properties and vaccine potential of the staphylococcal poly-N-acetyl glucosamine surface polysaccharide. Vaccine. Feb. 17, 2004;22(7):872-9. Review.

Mikayama et al., Molecular cloning and functional expression of a cDNA encoding glycosylation-inhibiting factor. Proc Natl Acad Sci U S A. Nov. 1, 1993;90(21):10056-60.

Sack, Deadly Bacteria Found to Be More Common. New York Times. Oct. 17, 2007. Available at http://www.nytimes.com/2007/10/17/health/17infect.html?pagewanted=prin. Last accessed Apr. 30, 2010. 3 pages.

Zeller et al., JAMA patient page. MRSA infections. JAMA. Oct. 17, 2007;298(15):1826.

[No Author Listed] Adis R&D Profile Drug in R&D. Adis International. 2003;4(6):383-5. Available at http://www.ingentaconnect.com/content/adis/rdd//2003/00000004/00000006/art00013. Last accessed Nov. 11, 2010. Abstract only.

Burgeot et al., Immunopotentiation of *Staphylococcus aureus* type 5 capsular polysaccharide co-entrapped in liposomes with alpha-toxin. Vaccine. Feb. 28, 2001;19(15-16):2092-9. Abstract only.

Fattom et al., Comparative immunogenicity of conjugates composed of the *Staphylococcus aureus* type 8 capsular polysaccharide bound to carrier proteins by adipic acid dihydrazide or N-succinimidyl-3-(2-pyridyldithio)propionate. Infect Immun. Feb. 1992;60(2):584-9.

Fattom et al., Development of StaphVAX, a polysaccharide conjugate vaccine against *S. aureus* infection: from the lab bench to phase III clinical trials. Vaccine. Feb. 17, 2004;22(7):880-7. Abstract only.

Jones, Revised structures for the capsular polysaccharides from *Staphylococcus aureus* Types 5 and 8, components of novel glycoconjugate vaccines. Carbohydr Res. May 2, 2005;340(6):1097-106. Abstract only.

Propst et al., Abstracts of the General Meeting of the American Society for Microbiology. 1998;42:242.

Skurnik et al., Animal and human antibodies to distinct *Staphylococcus aureus* antigens mutually neutralize opsonic killing and protection in mice. J Clin Invest. Sep. 1, 2010;120(9):3220-33. doi: 10.1172/JCI42748. Epub Aug. 25, 2010.

[No Author Listed] Illustrated Stedman's Medical Dictionary, 24th Edition, Williams and Wilkens. London. 1982:707.

[No Author Listed] The New Riverside University Dictionary. The Riverside Publishing Company.1984:933.

Gehron et al., Determination of the gram-positive bacterial content of soils and sediments by analysis of teichoic acid components. J Microbiol Methods. 1984;2:165-76.

Kille et al., Sucralose: assessment of teratogenic potential in the rat and the rabbit. Food Chem Toxicol. 2000;38 Suppl 2:S43-52.

Maira-Litrán et al., Comparative opsonic and protective activities of *Staphylococcus aureus* conjugate vaccines containing native or deacetylated Staphylococcal Poly-N-acetyl-beta-(1-6)-glucosamine Infect Immun. Oct. 2005;73(10):6752-62. Erratum: Infect Immun. Nov. 2005;73(11):7789.

Peterson et al., The key role of peptidoglycan in the opsonization of *Staphylococcus aureus*. J Clin Invest. Mar. 1978;61(3):597-609.

Pollack et al., Functional properties of isotype-switched immunoglobulin M (IgM) and IgG monoclonal antibodies to Pseudomonas aeruginosa lipopolysaccharide. Infect Immun. Nov. 1995;63(11):4481-8.

Preston et al., Production and characterization of a set of mouse-human chimeric immunoglobulin G (IgG) subclass and IgA monoclonal antibodies with identical variable regions specific for Pseudomonas aeruginosa serogroup O6 lipopolysaccharide. Infect Immun. Sep. 1998;66(9):4137-42.

Preston et al., Prophylactic and therapeutic efficacy of immunoglobulin G antibodies to Pseudomonas aeruginosa lipopolysaccharide against murine experimental corneal infection. Invest Ophthalmol Vis Sci. Jun. 1997;38(7):1418-25.

Sanger et al., A microapparatus for liquid hydrogen fluoride solvolysis: sugar and amino sugar composition of Erysiphe graminis and Triticum aestivum cell walls. Anal Biochem. Jan. 1983;128(1):66-70.

Soell et al., Capsular polysaccharide types 5 and 8 of *Staphylococcus aureus* bind specifically to human epithelial (KB) cells, endothelial cells, and monocytes and induce release of cytokines. Infect Immun. Apr. 1995;63(4):1380-6.

Sundgren et al., Varied presentation of the Thomsen-Friedenreich disaccharide tumor-associated carbohydrate antigen on gold nanoparticles. Carbohydr Res. Jul. 21, 2008;343(10-11):1594-604. Epub May 8, 2008. Published online May 8, 2008. doi: 10.1016/j.carres.2008.05.003. 16 pages.

Thoma et al., Novel glycodendrimers self-assemble to nanoparticles which function as polyvalent ligands in vitro and in vivo. Angew Chem Int Ed Engl. Sep. 2, 2002;41(17):3195-8.

Thoma et al., Synthesis of oligosaccharide-polylysine conjugates: A well characterized sialyl lewis polymer for elisa. J Am Chem Soc. 1997;119(31):7414-5.

Von Eiff et al., Distribution of capsular and surface polysaccharide serotypes of *Staphylococcus aureus*. Diagn Microbiol Infect Dis. Jul. 2007;58(3):297-302. Epub Mar. 26, 2007.

Wicken et al., Characterization of group N streptococcus lipoteichoic acid. Infect Immun May 1975;11(5):973-81.

Supplementary European Search Report for Application No. EP 03786713 dated Dec. 6, 2006.

[No Author Listed] ATCC Catalogue website 2001; ATCC No. 35984.

[No Author Listed] ATCC Catalogue: Bacteria and Bacteriophages; 1992; 18th Edition; p. 301.

Fridman et al., One-pot synthesis of glucosamine oligosaccharides. Org Lett. Jan. 24, 2002;4(2):281-3.

Gening et al., Synthetic {beta}-(1->6)-linked N-acetylated and nonacetylated oligoglucosamines used to produce conjugate vaccines for bacterial pathogens. Infect Immun. Feb. 2010;78(2):764-72. Doi: 10.1128/IAI.01093-09. Epub Nov. 30, 2009.

Gening et al., Synthesis of beta-(1-->6)-linked glucosamine oligosaccharides corresponding to fragments of the bacterial surface polysaccharide poly-N-acetylglucosamine. Carbohydr Res. Feb. 26, 2007;342(3-4):567-75. Epub Sep. 6, 2006.

Gening et al., The study of the reaction of terminated oligomerization in the synthesis of oligo-(beta1-6)-glucosamines. Bioorg Khim. Jul.-Aug. 2006;32(4):432-43. Published in English in Russian Journal of Biorganic Chemistry, 2006;32(4):389-99.

Grachev et al., NMR and conformational studies of linear and cyclic oligo-(1→6)-β-D-glucosamines Carbohydr Res. Nov. 8, 2011;346(15):2499-510. Epub Sep. 5, 2011.

Hermanson, Bioconjugate Techniques, Academic Press, XP-002473633; pp. 34, 187-188, 218-220, 228-248 (1996) (pp. 34, 187-248).

O'Brien et al., Production of antibodies to *Staphylococcus aureus* serotypes 5, 8, and 336 using poly(DL-lactide-co-glycolide) microspheres. J Dairy Sci. Aug. 2000;83(8):1758-66.

Skurnik et al., Targeting pan-resistant bacteria with antibodies to a broadly conserved surface polysaccharide expressed during infection. J Infect Dis. Jun. 2012;205(11):1709-18. Doi: 10.1093/infdis/jis254. Epub Mar. 23, 2012.

Yang et al., A practical synthesis of a (1-->6)-linked beta-D-glucosamine nonasaccharide. Carbohydr Res. Mar. 14, 2003;338(6):495-502.

Yang et al., Synthesis of biantennary beta-D-(1-->6) glucosamine oligosaccharides. Carbohydr Res. Jun. 16, 2003;338(12):1313-8.

Yudina et al., Synthesis of five nona-β-(1→6)-d-glucosamines with various patterns of N-acetylation corresponding to the fragments of

(56) References Cited

OTHER PUBLICATIONS exopolysaccharide of *Staphylococcus aureus*. Carbohydr Res. May 15, 2011;346(7):905-13. Epub Feb. 23, 2011.
U.S. Appl. No. 08/336,688, filed Nov. 7, 1994, Granted, U.S. Pat. No. 5,980,910.
U.S. Appl. No. 10/093,582, filed Mar. 8, 2002, Granted, U.S. Pat. No. 6,743,431.
U.S. Appl. No. 09/771,003, filed Jan. 26, 2001, Granted, U.S. Pat. No. 7,252,828.
U.S. Appl. No. 11/645,220, filed Dec. 22, 2006, Granted, U.S. Pat. No. 8,663,654.
U.S. Appl. No. 10/712,391, filed Nov. 12, 2003, Granted, U.S. Pat. No. 7,723,087.
U.S. Appl. No. 11/111,688, filed Apr. 21, 2005, Granted, U.S. Pat. No. 7,786,255.
U.S. Appl. No. 12/824,510, filed Jun. 28, 2010, Granted, U.S. Pat. No. 8,084,595.
U.S. Appl. No. 13/103,532, filed May 9, 2011, Granted, U.S. Pat. No. 8,252,894.
U.S. Appl. No. 13/334,775, filed Dec. 22, 2011, Granted, U.S. Pat. No. 8,350,017.
U.S. Appl. No. 13/334,807, filed Dec. 22, 2011, Granted, U.S. Pat. No. 8,435,515.
U.S. Appl. No. 13/334,840, filed Dec. 22, 2011, Granted, U.S. Pat. No. 8,461,319.
U.S. Appl. No. 13/334,869, filed Dec. 22, 2011, Granted, U.S. Pat. No. 8,410,249.
U.S. Appl. No. 13/735,531, filed Jan. 7, 2013, Granted, U.S. Pat. No. 8,912,314.
U.S. Appl. No. 14/548,173, filed Nov. 19, 2014, Pending.
U.S. Appl. No. 13/055,178, filed Mar. 2, 2011, Granted, U.S. Pat. No. 8,492,364.
U.S. Appl. No. 13/924,435, filed Jun. 21, 2013, Published 2014-0037633.
U.S. Appl. No. 14/404,303, filed Nov. 26, 2014, Published 2015-0165016.
Bobrov et al., Insights into Yersinia pestis biofilm development: topology and co-interaction of Hms inner membrane proteins involved in exopolysaccharide production. Environ Microbiol. Jun. 2008;10(6):1419-32. doi: 10.1111/j.1462-2920.2007.01554.x.
Conover et al., The Bps polysaccharide of Bordetella pertussis promotes colonization and biofilm formation in the nose by functioning as an adhesin. Mol Microbiol. Sep. 2010;77(6):1439-55. doi: 10.1111/j.1365-2958.2010.07297.x.
Cywes-Bentley et al., Antibody to a conserved antigenic target is protective against diverse prokaryotic and eukaryotic pathogens. Proc Natl Acad Sci U S A. Jun. 11, 2013;110(24):E2209-18. doi: 10.1073/pnas.1303573110. Epub May 28, 2013.
Parise et al., Role of a putative polysaccharide locus in Bordetella biofilm development. J Bacteriol. Feb. 2007;189(3):750-60.
Blixt et al., Solid-Phase Enzymatic Synthesis of a Lewis a Trisaccharide Using an Acceptor Reversibly Bound to Sepharose, J Carb Chem. Feb. 1997;16(2):143-54. doi: 10.1080/07328309708006516.
Wright et al., Preparation of synthetic glycoconjugates as potential vaccines against Shigella flexneri serotype 2a disease. Org Biomol Chem. May 21, 2004;2(10):1518-27. Epub Apr. 26, 2004.
[No Author Listed] Pneumococcal Disease, Transmission and Those at High Risk. CDC Control and Prevention. Sep. 2017. Available at http://www.cdc.gov/pneumococcal/about/risk-transmission.html. Last accessed Mar. 8, 2018. pp. 1-2.
[No Author Listed] Five Surprising Facts about Pneumococcal Pneumonia. American Lung Association. Nov. 2017. Available at http://www.lung.org/about-us/media/top-stories/five-surprising-facts-about-pneumococcal-pneumonia.html. Last accessed Mar. 8, 2018. pp. 1-3.
[No Author Listed] Stedman's Medical Dictionary. $24^{th}$ Edition. 1982. p. 707.
Chiavolini et al., Animal models of *Streptococcus pneumoniae* disease. Clin Microbiol Rev. Oct. 2008;21(4):666-85. doi: 10.1128/CMR.00012-08. Review.
Cywes-Bentley et al., Supporting Information for Antibody to a conserved antigenic target is protective against diverse prokaryotic and eukaryotic pathogens. Proc Natl Acad Sci U S A. Jun. 11, 2013;110(24):E2209-18. doi: 10.1073/pnas.1303573110. Epub May 28, 2013.
Hinnebusch et al., Yersinia pestis Biofilm in the Flea Vector and Its Role in the Transmission of Plague. Curr Top Microbiol Immunol. 2008; 322: 229-48.
Skurnik et al., The exceptionally broad-based potential of active and passive vaccination targeting the conserved microbial surface polysaccharide PNAG. Expert Rev Vaccines. Aug. 2016;15(8):1041-53. doi: 10.1586/14760584.2016.1159135. Epub Mar. 16, 2016.
Vlock et al., Pre-clinical and initial phase I evaluations of a fully human monoclonal antibody directed against the PNAG surface polysaccharide on *Staphylococcus aureus* In: Abstract of the 50th Interscience conference on Antimicrobial Agents and Chemotherapy. Abstract G1-1654. Sep. 12-15, 2010; p. 329.
Zaidi et al., Microbiota-driven immune cellular maturation is essential for antibody-mediated adaptive immunity to *Staphylococcus aureus* infection in the eye. Infect Immun. Aug. 2014;82(8):3483-91. doi: 10.1128/IAI.01951-14. Epub Jun. 9, 2014.
Zhao et al., Efficacy of Antibody to PNAG Against Keratitis Caused by Fungal Pathogens. Invest Ophthalmol Vis Sci. Dec. 1, 2016;57(15):6797-6804. doi: 10.1167/iovs.16-20358.
Kaplan et al., Genes involved in the synthesis and degradation of matrix polysaccharide in Actinobacillus actinomycetemcomitans and Actinobacillus pleuropneumoniae biofilms. J Bacteriol. Dec. 2004;186(24):8213-20.

\* cited by examiner

POLYSACCHARIDE VACCINE FOR STAPHYLOCOCCAL INFECTIONS

RELATED APPLICATIONS

This application claims priority under 35 U.S.C. § 119(e) to U.S. Provisional Application Ser. No. 60/425,425, filed Nov. 12, 2002, and entitled "POLYSACCHARIDE VACCINE FOR STAPHYLOCOCCAL INFECTIONS", the contents of which are herein incorporated by reference in their entirety.

GOVERNMENT SUPPORT

This invention was made with government support under AI046706 awarded by National Institutes of Health. The government has certain rights in the invention.

FIELD OF THE INVENTION

The present invention relates to polysaccharide compositions useful for inducing immunity for the prevention and treatment of Staphylococcal infections. The invention also relates to methods of making and using polysaccharide based antigens, related antibodies and diagnostic kits and for inducing active and passive immunity using the polysaccharide material and antibodies thereto.

BACKGROUND OF THE INVENTION

Staphylococci are gram-positive bacteria which normally inhabit and colonize the skin and mucus membranes of humans. If the skin or mucus membrane becomes damaged during surgery or other trauma, the Staphylococci may gain access to internal tissues causing infection to develop. If the Staphylococci proliferate locally or enter the lymphatic or blood system, serious infectious complications such as those associated with Staphylococcal bacteremia may result. These complications include septic shock, endocarditis, arthritis, osteomyelitis, pneumonia, and abscesses in various organs.

Staphylococci include both coagulase-positive organisms that produce a free coagulase and coagulase-negative organisms that do not produce this free coagulase. *Staphylococcus aureus* is the most common coagulase-positive form of Staphylococci. *S. aureus* generally causes infection at a local site, either extravascular or intravascular, which ultimately may result in bacteremia. *S. aureus* is also a leading cause of acute osteomyelitis, and causes Staphylococcal pneumonia infections. Additionally, *S. aureus* is responsible for approximately 1-9% of the cases of bacterial meningitis and 10-15% of brain abscesses.

There are at least twenty-one known species of coagulase-negative Staphylococci, including *S. epidermidis, S. saprophyticus, S. hominis, S. warneri, S. haemolyticus, S. saprophiticus, S. cohnii, S. xylosus, S. simulans*, and *S. capitis. S. epidermidis* is the most frequent infection-causing agent associated with intravenous access devices, and the most frequent isolate in primary nosocomial bacteremias. *S. epidermidis* is also associated with prosthetic valve endocarditis.

*Staphylococcus* is also a common source of bacterial infection in animals. For instance, Staphylococcal mastitis is a common problem in ruminants such as cattle, sheep, and goats. The disease is generally treated with antibiotics to reduce the infection but the treatment is a costly procedure and still results in a loss of milk production. The most effective vaccines identified to date are live, intact *S. aureus* vaccines administered subcutaneously. The administration of live vaccines, however, is associated with the risk of infection. For that reason, many researchers have attempted to produce killed *S. aureus* vaccines and/or to isolate capsular polysaccharides or cell wall components which will induce immunity to *S. aureus*. None of these attempts, however, has been successful.

SUMMARY OF THE INVENTION

The present invention relates to methods and products useful for immunization of humans and animals against infection by coagulase-negative and coagulase-positive Staphylococci. It has been discovered, according to the invention, that a poly N-acetyl glucosamine (PNAG) surface polysaccharide from Staphylococci, such as *S. aureus* and *S. epidermis*, that is poorly substituted with acetate residues, is highly immunogenic in vivo and preferentially elicits antibodies that mediate opsonic killing and protection from infection. This polysaccharide is therefore useful, inter alia, in the generation of immune responses, including antibody dependent immune responses, to Staphylococci.

In one aspect, the invention provides a composition comprising an isolated polysaccharide comprising a β-1,6-glucosamine polymer, having a length of at least two monomeric units, wherein less than 50% of glucosamine amino groups are substituted with acetate. In one aspect, the composition is sterile (e.g., it would be suitable for in vivo injection). In another aspect, the invention provides a composition comprising an isolated polysaccharide comprising a β-1,6-glucosamine polymer, having a length of at least two monomeric units, wherein less than 50% of glucosamine amino groups are substituted with acetate and wherein the polysaccharide is conjugated to a carrier compound.

As used throughout, "a polysaccharide of the invention" refers to Staphylococcal poly-N-acetyl glucosamine (PNAG) surface polysaccharide having less than 50% acetate substitutions. This polysaccharide is referred to herein as deacetylated PNAG (dPNAG). It is to be understood that dPNAG may be wholly or partially deacetylated, provided that the range of acetylation is from 0 to less than 50%. As used herein, native PNAG is a mixture of PNAG forms with varying degrees of acetylation. Native PNAG may include dPNAG, however it is present in a mixture with highly acetylated forms of PNAG. As used herein, a "highly acetylated" form of PNAG is a PNAG having greater than 50% acetate substitutions.

Several embodiments apply equally to the various aspects of the invention. These embodiments are recited below.

In one embodiment, the isolated polysaccharide is defined by the following structure:

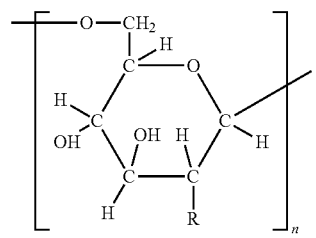

wherein n is an integer greater than or equal to four, R is selected from the group consisting of —NH—CO—CH$_3$ and —NH$_2$, and less than 50% of the R groups are —NH—

CO—CH$_3$. According to some aspects of the invention in which the polysaccharide is conjugated to a carrier compound or a linker joined to a carrier compound, n can be 2, 3, 4 or greater.

In one embodiment, the polysaccharide has a molecular weight of at least 800 Daltons, while in other embodiments, the molecular weight is at least 1000 Daltons. In still further embodiments, the molecular weight is selected from the group consisting of at least 1200 Daltons, at least greater than 2000 Daltons, at least 2500 Daltons, at least 5000 Daltons, at least 7500 Daltons, at least 10,000 Daltons, at least 25,000 Daltons, at least 50,000 Daltons, at least 75,000 Daltons, and at least 100,000 Daltons. In still further embodiments, the molecular weight is selected from the group consisting of at least 125,000 Daltons, at least 150,000 Daltons, at least 200,000 Daltons, at least 250,000 Dalton, at least 300,000 Daltons, at least 350,000 Daltons, at least 400,000 Daltons, at least 450,000 Daltons, and at least 500,000 Daltons.

The isolated polysaccharide may have a length of at least two, at least three, at least four, at least five, or at least six monomeric units. In other embodiments, the length of the polysaccharide is selected from the group consisting of at least 6, at least 10, at least 20, at least 50, at least 100, at least 200, at least 300, at least 400, and at least 500 monomer units. In other embodiments, equal to or less than 45%, equal to or less than 40%, equal to or less than 35%, equal to or less than 30%, equal to or less than 25%, equal to or less than 20%, equal to or less than 15%, equal to or less than 10%, equal to or less than 5%, or equal to or less than 1% of glucosamine amino groups (or R groups) are substituted with acetate. In still other embodiments, none of the glucosamine amino groups is substituted with acetate. The dPNAG may refer to any of these.

Accordingly, the polysaccharide may be a hetero-substituted polymer, wherein the R groups are a mixture of acetate substitutions (i.e., —NH—CO—CH$_3$) and unsubstituted amine (i.e., —NH$_2$) groups, provided that less than 50% of these groups are substituted with acetate. The polysaccharide can also be homo-substituted if all of the R groups are amines (i.e., none is acetate-substituted).

In some embodiments of the invention, the isolated polysaccharide may be conjugated to a carrier compound. The carrier compound may be conjugated to the polysaccharide via a linker. The carrier compound may be a peptide carrier, but it is not so limited.

In these and other embodiments, the composition comprising the isolated polysaccharide may further comprise a pharmaceutically acceptable carrier.

In some embodiments, the composition is at least 90% pure, at least 95% pure, at least 97% pure, or at least 99% pure (i.e., at least 90%, at least 95%, at least 97% or at least 99% of the polysaccharide present in the composition is dPNAG). In yet other embodiments, the composition is substantially free of phosphate or teichoic acid. Preferably, the composition is substantially free of polysaccharides having greater than 50%, greater than 75%, or greater than 90% acetate substitution at the glucosamine amino (R) group.

In some embodiments, the polysaccharide consists of the following structure:

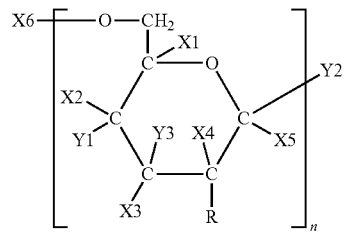

wherein each of X1, X2, X3, X4, X5 and X6 is either H, a carrier compound, or a linker joined to a carrier compound; and each of Y1, Y2 and Y3 is either OH, a carrier compound, or a linker joined to a carrier compound. In some embodiments, only one carrier compound or linker joined to a carrier compound is conjugated to the structure. In other embodiments, only one of X1, X2, X3, X4, X5 or X6 is conjugated to a carrier compound or a linker joined to a carrier compound. In still other embodiments, only one of Y1, Y2 or Y3 is conjugated to a carrier compound or linker joined to a carrier compound. In still other embodiments, the carrier compound or linker conjugated thereto is conjugated at only one of the X1, X2, X3, X4, X5, X6, Y1, Y2 or Y3 positions. The carrier compound may be a polysaccharide. In other embodiments, the carrier molecule is a polysaccharide optionally substituted directly, or through a linker, with one or more carrier compounds, such as other polysaccharides, peptides, and the like. In some embodiments, the carrier polysaccharide is not an N-acetyl beta ((3) 1-6 glucosamine. According to some aspects of the invention in which X is a carrier compound or a linker joined to a carrier compound, n can be 2, 3, 4 or greater.

The invention provides pharmaceutical compositions comprising any of the polysaccharides of the invention, which may be used as vaccines. These compositions comprise the polysaccharide in an amount effective to stimulate an immune response, such as an antigen-specific immune response. The vaccine composition may further comprise a pharmaceutically acceptable carrier and/or an adjuvant. The pharmaceutical composition may contain the polysaccharide conjugated to a carrier compound, either directly or through a linker.

Other aspects of the invention provide methods for making the polysaccharides of the invention. These methods are described below.

In one aspect, the invention provides an isolated polysaccharide prepared according to the following method: ethanol precipitating a crude polysaccharide preparation from a concentrated bacterial cell body preparation; concurrently digesting the crude polysaccharide with lysozyme and lysostaphin followed by sequential digestion with a nuclease and proteinase K to form a digested polysaccharide preparation; size fractionating the digested polysaccharide preparation; isolating an acetylated polysaccharide fraction; and de-acetylating the acetylated polysaccharide to produce a deacetylated polysaccharide (i.e., a polysaccharide having less than 50% acetate substitution).

In another aspect, the invention also provides a polysaccharide antigen comprising a polysaccharide prepared according to the following method: preparing an impure polysaccharide from a bacterial culture; incubating the impure polysaccharide with an acid or a base to produce a semi-pure polysaccharide; neutralizing the preparation; and incubating the neutralized preparation in hydrofluoric acid. In one embodiment, the method further involves isolating an acetylated polysaccharide from the preparation, and de-acetylating the acetylated polysaccharide to produce a deacetylated polysaccharide. In one embodiment, the acetylated polysaccharide is chemically de-acetylated, to a desired degree that is less than 50%. In another embodiment, the acetylated polysaccharide is de-acetylated by incubation with a basic solution, to a desired degree that is less than 50%. In still another embodiment, the acetylated polysaccharide is enzymatically de-acetylated.

Various embodiments apply to the foregoing methods. Some of these additional embodiments are recited below. The bacterial culture may be a coagulase-negative or a coagulase-positive *Staphylococcus* culture. The bacterial culture may be a *Staphylococcus aureus* culture or a *Staphylococcus epidermidis* culture. In another embodiment, the polysaccharide preparation is size fractionated using a column.

An example of a preparation of the polysaccharide of the invention is as follows: A bacterial culture is incubated with a strong base or a strong acid to make an acid or a base solution. The acid or base solution is then neutralized to pH 2 to produce a crude antigen suspension. The crude antigen suspension is dialyzed against a solution such as deionized water, and insoluble crude antigen is collected. The insoluble crude antigen can be lyophilized and then resuspended in a buffer. The buffer can be selected from the group consisting of 50 mM PBS and 100 mM Tris with 150 mM NaCl. The strong base or acid can be greater than 1 N NaOH or 1 M HCl. In some embodiments, the strong base or acid is 5 N NaOH or 5 M HCl. In another embodiment, the bacterial culture extract is stirred in a strong base or acid for 18-24 hours. The strong base or acid extraction may be repeated. The method further involves treating the antigen preparation to remove amino-linked acetate groups until a desired degree of acetate substitution is reached, thereby producing the deacetylated PNAG. De-acetylation can be effected either chemically or enzymatically. As an example, the antigen preparation can be incubated at 37° C. for 2-20 hours in 1.0 N NaOH. The incubation can also be performed in weaker basis for longer times or at higher temperatures or in stronger bases for shorter times or at lower temperatures.

The foregoing methods can alternatively involve isolating a fraction from the preparation having less than 50% acetate substitutions, without the need for additional deacetylation.

The invention, in yet another aspect, provides methods for making pharmaceutical compositions. In one embodiment, the polysaccharide is combined with a pharmaceutically acceptable carrier and/or adjuvant. In another embodiment, the polysaccharide is conjugated to a carrier compound, either directly or through a linker, and then optionally combined with a pharmaceutically acceptable carrier and/or an adjuvant.

Any of the deacetylated polysaccharides described herein (i.e., dPNAG) can be used in the therapeutic or prophylactic methods of the invention.

In another aspect, the invention provides a method for preventing a *Staphylococcus* infection in a subject, preferably a non-rodent subject. The invention involves administering to a subject in need thereof an effective amount for inducing an immune response against *Staphylococcus* of any of the polysaccharides of the invention. In some embodiments the *Staphylococcus* is *Staphylococcus aureus*, and in others the *Staphylococcus* is *Staphylococcus epidermidis*.

The subject is any subject that can be infected with *Staphylococcus* and preferably is not a rodent. In some embodiments, the subject is a human subject, and in other embodiments the subject is a primate, horse, cow, swine, goat, sheep, dog or cat.

In some embodiments, the subject is at risk of exposure to *Staphylococcus*, and in other embodiments, the subject has been exposed to *Staphylococcus*. In some embodiments, the subject is a human over 60 years of age. The subject may be one that is healthy. In some embodiments, the subject has not received a medical device implant.

Preferably, the polysaccharide is formulated as a vaccine, as described herein or as is known in the art. In a related embodiment, the polysaccharide is administered with an adjuvant. In other embodiments, the polysaccharide is administered systemically to the subject. The antigen may conjugated to a carrier compound. In some embodiments, the carrier compound is a peptide carrier although it is not so limited.

In another aspect, the invention provides a method for inducing active immunity to a Staphylococcal infection in a subject. The method includes the step of administering to a subject an effective amount for inducing active immunity to a Staphylococcal infection of any of the foregoing polysaccharide-containing compositions. In one embodiment, the method is a method for inducing immunity to infection by *Staphylococcus aureus*. In another embodiment, the method is a method for inducing immunity to infection by *Staphylococcus epidermidis*.

A method for producing polyclonal or monoclonal antibodies is provided according to another aspect of the invention. The method involves administering to a subject an adjuvant and any of the polysaccharides of the invention in an effective amount for producing antibodies specific for *Staphylococcus*, and isolating antibodies from the subject. In these as well as other aspects of the invention, the polysaccharide is used as an antigen. In one embodiment the subject is human, while in others the subject is a non-human subject such as a rabbit, mouse or rat. The method may further comprise purifying the antibody.

In another aspect, the invention provides a method for generating monoclonal antibodies comprising administering to a subject an effective amount, for producing antibodies specific for *Staphylococcus*, of an isolated polysaccharide of the invention, and an adjuvant, harvesting spleen cells from the subject, fusing spleen cells from the subject to myeloma cells, and harvesting antibody production from a fusion subclone.

According to yet another aspect of the invention, a method is provided for identifying a monoclonal antibody specific for a polysaccharide of the invention. The method involves inducing an immune response to the antigen in a non-human subject, isolating antibody producing cells from the subject, producing immortalized cells from the antibody producing cells, and testing the ability of the immortalized cells to produce the monoclonal antibody using a polysaccharide of the invention. The method, in one embodiment, also includes the step of isolating a monoclonal antibody from the supernatant of the immortalized cells.

The invention further provides a composition comprising an isolated binding agent that binds selectively to an isolated polysaccharide of the invention. In one embodiment, the isolated binding agent is a peptide. The peptide maybe an antibody, or a fragment thereof. The antibody may be a polyclonal antibody. The antibody may be a humanized antibody or a chimeric antibody. In some important embodiments, the antibody is a human antibody. In some embodiments, the isolated binding agent binds specifically to dPNAG. In other embodiments, the isolated binding agent binds to both dPNAG and highly acetylated forms of PNAG.

In some embodiments, the isolated binding agent is conjugated to a detectable label. The detectable label may be selected from the group consisting of a radioactive label, an enzyme, a biotin molecule, an avidin molecule or a fluorochrome. The isolated binding agent may be conjugated to a bactericide, such as an antibiotic.

According to another aspect of the invention, a method is provided for inducing passive immunity to *Staphylococcus* infection in a subject. The infection may be a *Staphylococcus aureus* infection or a *Staphylococcus epidermis* infection, but is not so limited. The method includes the step of administering to a subject an effective amount, for inducing opsonization of *Staphylococcus*, of one of the foregoing antibodies that bind to dPNAG.

The foregoing methods intended for prevention of a Staphylococcal infection can be performed on subjects at risk of developing such an infection. These methods can similarly be applied to the treatment of subjects having a Staphylococcal infection. The prophylactic and therapeutic methods of the invention can be used in subjects having or at risk of having an infection from a bacterial species that expresses native PNAG.

In a further aspect, the invention provides a method for treating a subject having a *Staphylococcus* infection comprising administering an isolated binding agent that binds to an isolated polysaccharide of the invention to a subject in an amount effective to inhibit the *Staphylococcus* infection. In important embodiments, the binding agent binds to highly acetylated forms of PNAG as well as dPNAG.

In one embodiment, the *Staphylococcus* infection is selected from the group consisting of *Staphylococcus epidermidis* infection and *Staphylococcus aureus* infection. In another embodiment, the isolated binding agent is conjugated to a bactericide, such as an antibiotic.

Another aspect of the invention provides a method for evaluating the ability of a polysaccharide to protect against Staphylococcal infection in a subject. The method involves administering to the subject an effective amount of the polysaccharide, wherein the polysaccharide induces active immunity, exposing the subject to a *Staphylococcus*, and testing for the presence of *Staphylococcus* in the subject.

In yet another aspect, the invention provides a method for identifying the presence of dPNAG in a sample, comprising contacting a sample with an isolated binding agent that binds to dPNAG; and detecting binding of the isolated binding agent to the sample. Binding of the isolated binding agent to the sample indicates the presence of dPNAG in the sample. If the binding agent also binds PNAG, then the method can also be used to detect the presence of PNAG in the sample. In one embodiment, the sample is a biological sample from a subject. The biological sample may be selected from the group consisting of urine, blood, pus, skin, sputum, joint fluid, lymph and milk. In one embodiment, the isolated binding agent is conjugated to a detectable label such as those described herein. A sample may also be derived from a swab of an implantable or implanted medical device.

Each of the limitations of the invention can encompass various embodiments of the invention. It is therefore anticipated that each of the limitations of the invention involving any one element or combinations of elements can be included in each aspect of the invention.

BRIEF DESCRIPTION OF THE SEQUENCE LISTING

SEQ ID NO:1 is the nucleotide sequence of the ica locus from *S. aureus* which has been deposited in GenBank under accession number AF086783.

DETAILED DESCRIPTION OF THE INVENTION

Figure 1:
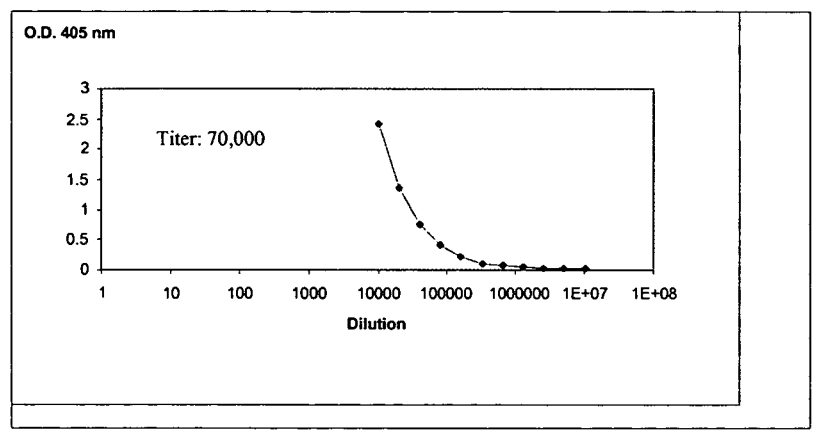
FIG. 1 shows the binding of antibody to native PNAG. The antibody was raised to native PNAG conjugated to diphtheria toxoid.

The invention relates to polysaccharide antigens derived from Staphylococcal bacteria. These antigens are useful for inducing immunity to bacterial infection and also for producing antibodies for diagnostic and therapeutic purposes.

The instant invention is based in part on the finding that poorly acetylated (i.e., deacetylated) poly-N-acetyl glucosamine (PNAG), referred to herein as dPNAG, is highly immunogenic and thus represents a suitable vaccine candidate for stimulating protective immune responses in vivo. A deacetylated PNAG is one having less than 50% of its amino groups substituted with acetate. In some preferred embodiments, there are 35% or fewer acetate substituents, while in others there are 15% or fewer acetate substituents. It has been further discovered, according to the invention, that dPNAG is better able to elicit opsonic protective antibodies than is native PNAG. "Native" PNAG refers to the naturally occurring mixture of PNAG with a range of acetylation levels ranging from 0-100%. dPNAG can be derived from native PNAG using the de-acetylation methods described herein. The antibodies prepared against dPNAG are thus effective against Staphylococci such as *S. aureus* and *S. epidermidis*. Accordingly, it has been discovered according to the invention that the extent of acetylation influences the level of immune response induced upon antigen administration in vivo. The antibodies elicited following dPNAG administration recognize dPNAG and in important embodiments also recognizes highly acetylated forms of PNAG.

The invention provides compositions of isolated dPNAG, methods of isolating and in some instances purifying dPNAG, as well as methods of use, including in vivo therapeutic, prophylactic and diagnostic methods. As used herein, the dPNAG may be referred to as dPNAG antigen. These latter terms are intended to be interchangeable. The invention also provides pharmaceutical compositions of dPNAG which may be used as vaccines.

In some aspects, dPNAG has the following structure:

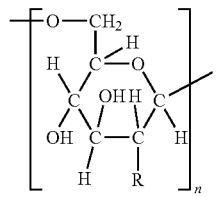

where, n is an integer ranging from 2 to greater than or equal to 300, R is selected from the group consisting of —NH—CO—CH$_3$ and —NH$_2$, provided that less than 50% of the R groups are —NH—CO—CH$_3$. dPNAG has a beta (β) 1-6 linkage (i.e., it is comprised of glucosamine monomer units linked together by beta (β) 1-6 linkages).

dPNAG may be a homo-polymer if all the R groups are unsubstituted (i.e., R=NH$_2$). A homo-polymer is one in which the R groups of the glucosamine residues are identical. dPNAG can also be a hetero-polymer with a mixture of —NH$_2$ and —NH—CO—CH$_3$ groups at the R position provided that less than 50% of R groups are substituted with acetate. Depending on the embodiments, less than 49%, less than 45%, less than 40%, less than 35%, less than 30%, less than 25%, less than 20%, less than 15%, less than 10%, less than 5%, or less than 1% of R groups may be substituted with acetate.

The size of dPNAG varies greatly, and depends upon whether dPNAG is conjugated to a carrier compound, as described herein. In some aspects, dPNAG antigen has a molecular weight of at least 100,000 Daltons. In other aspects, dPNAG antigen has a molecular weight of less than 2000 Daltons. The molecular weight of PNAG may be at least 200 Daltons, or at least 400 Daltons, or at least 600 Daltons, or at least 800 Daltons. Lower molecular weight dPNAG can be used according to the invention, preferably when conjugated to a carrier compound. These dPNAG can be as small as 2-3 monomer units, but preferably are at least 4-6 monomer units in length. The corresponding molecular weights for these are approximately 400, 600, 800, 1000 and 1200 Daltons. Polysaccharides between 500 and 20,000,000 Daltons will be typical.

As will be understood, the value of n in the above structure has an impact on the molecular weight of the antigen. If n is equal to or greater than 300, then the molecular weight of the minimal polysaccharide in the structure is 60,918 Daltons (300 units×203 Daltons/unit+18 Daltons for the substituents on the terminal residues). If the antigen has a minimum molecular weight of 100,000 Daltons, then either the polysaccharide has more than 300 units, or the polysaccharide is conjugated to a carrier compound which makes up for the difference in the molecular weight.

The invention provides both naturally occurring and synthetic forms of the dPNAG antigen. As used herein, the naturally occurring dPNAG is one that exists in or can be isolated or derived from naturally-occurring sources. dPNAG antigens are also provided in an isolated form. An isolated polysaccharide, such as isolated dPNAG, is one that has been removed and thus separated from the environment in which it normally exists. In some instances, an isolated polysaccharide is sufficiently separated from other compounds to be characterized structurally or functionally. For example, an isolated polysaccharide may be "sequenced" in order to determine its chemical composition.

dPNAG can be prepared from any bacterial strain carrying the ica locus. These strains include but are not limited to *S. epidermis* and *S. aureus*, and other strains (e.g., *S. carnosus*) that have been transformed with the genes in the ica locus. In particular, dPNAG can be prepared from specific strains including *S. epidermis* RP62A (ATCC number 35984), *S. epidermis* RP12 (ATCC number 35983), *S. epidermis* M187, *S. carnosus* TM300 (pCN27), *S. aureus* RN4220 (pCN27), and *S. aureus* MN8 mucoid.

One method involves incubating impure PNAG with a base or acid to produce a semi-pure PNAG preparation, neutralizing the preparation, and further treating the neutralized preparation to produce the dPNAG.

Impure native PNAG can be prepared by a variety of methods including extracting a crude native PNAG preparation from a bacterial culture, including cells and cell free culture supernatants, resulting in the isolation of a high molecular weight native PNAG-enriched material from the crude PNAG preparation, and obtained initially by precipitating an impure PNAG containing the high molecular weight PNAG-enriched material with a solvent such as methanol, ethanol, acetone or any other organic solvent known to one skilled in the art as being capable of causing the precipitation of polysaccharides from aqueous solutions. The steps of extracting the crude native PNAG preparation and isolating and precipitating the impure native PNAG antigen preparation are performed by any methods known in the art, such as those including U.S. Pat. No. 5,055,455. This impure material is then purified and de-acetylated to produce dPNAG of the invention.

The purification steps are achieved by incubating impure PNAG with bacterial enzymes that can digest biological materials, including cell-wall disrupting agents such as lysozyme, lysostaphin, and proteinase K, and nuclease enzymes such as DNase and RNase to digest DNA and RNA. This is followed by an addition of a solvent that will precipitate PNAG out of solution, collection of the precipitate and re-dissolution of PNAG in a base, such as NaOH or an acid such as HCl, followed by neutralization. The neutralization can be accomplished using a base if the incubation step was performed with an acid, or with an acid if the incubation step was performed with a base. The insoluble fraction from the neutral material is then treated, e.g., by incubation in hydrofluoric acid to produce a pure native PNAG antigen or by re-dissolution in buffers with a pH<4.0 followed by molecular sieve and/or ion-exchange chromatography.

Another isolation method includes the steps of extracting a crude PNAG suspension from a bacterial culture by incubating the bacteria with a strong base or acid. Preferably, the bacterial is stirred in the strong base or acid for at least 2 hours, and more preferably at least 5, 10, 15, 18 or 24 hours. The strong base or acid can be any type of strong base or acid, but preferably has a strength of at least 1 M NaOH or HCl. In some embodiments, the strong base or acid is 5 M NaOH or 5 M HCl. The acid or base solution is then subjected to centrifugation to collect the cell bodies. In some embodiments, the extraction procedure is repeated several times. The resultant acid or base solution is neutralized to approximately pH 7 and then dialyzed to produce insoluble impure PNAG.

dPNAG may be synthesized from naturally occurring polysaccharides that are greater than 50% acetate substituted. For instance, the dPNAG antigen may be synthesized by de-acetylating a heavily acetylated glucosamine polymer by chemical (e.g., base treatment) or by enzymatic means.

dPNAG antigens can also be synthesized de novo. (See, for example, Melean et al. Carbohydrate Research, 337: 1893-1916, 2002.) Starting materials include, but are not limited to polyglucose (i.e., dextran), polyglucosamines, such as chitin or chitosan, and polyglucosaminouronic acid. Polygalactosaminouronic acid may also be used to produce the dPNAG antigen of the invention. Polyglucosamines having various substituents may also be modified to produce the PNAG antigen. For instance, polysaccharide intercellular adhesin (PIA) is a heavily acetylated polymer of β-1-6 linked glucosamine residues. PIA has the following structure:

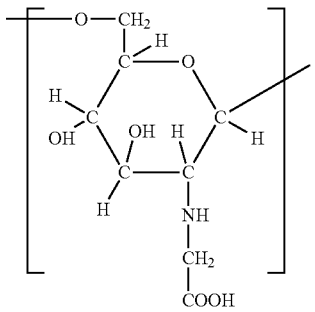

For those polysaccharides that contain imine moieties (C—NH), free amino groups can be formed by conventional chemistry techniques known to those of ordinary skill in the art. One suitable method involves the use of sodium borohydride. The imine group can be reduced with sodium borohydride to create a free amino group. This is done by adding in excess of 5 mg of borohydride to polysaccharide dissolved in distilled water while stirring at room temperature for 2 hours. The mixture is then dialyzed against water and freeze dried. (See, for example, DiFabio, et al. Biochem J., 1987 15; 244(1): 27-33).

The invention provides dPNAG preparations of varying purity. As used herein, a "pure dPNAG preparation" is a dPNAG preparation that has been isolated or synthesized and that is greater than 92% free of contaminants. These contaminants include heavily acetate substituted PNAG forms (i.e., greater than 50% acetate substitution), galactose, phosphate, teichoic acid, and the like. In some embodiments, dPNAG compositions are at least 93%, 94%, 95%, 96%, 97%, 98%, 99% free of contaminants or are 100% free of contaminants.

dPNAG compositions can also be referred to as "substantially free" of contaminants. A dPNAG composition substantially free of, for example, galactose indicates the presence of less than 10%, preferably less than 5%, or more preferably less than 1% galactose in a preparation containing dPNAG.

The degree of purity of the dPNAG composition can be assessed by any means known in the art. For example, the purity can be assessed by chemical analysis assays as well as gas chromatography and nuclear magnetic resonance to verify structural aspects of the material.

Another major contaminant of some dPNAG preparations can be phosphate-containing teichoic acid. The teichoic acid contamination can interfere with both the chemical characterization and the immunogenicity of the dPNAG antigen of the invention. The methods of the invention described herein are capable of producing an isolated dPNAG preparation that is substantially free of teichoic acid. A dPNAG preparation that is substantially free of teichoic acid is one which has less than 1.0% phosphate, and more preferably one that has less than 0.1% phosphate. The amount of phosphate present in the sample can be assessed by any means known in the art. The amount of phosphate contamination can be assessed using the methods described in Keleti, G. and W. H. Lederer, ((1974) *Handbook of Micromethods for the Biological Sciences* Van Nostrand Reinhold Co., New York), which is hereby incorporated by reference. Briefly, the assay is performed as follows: to 100 μg of sample 100 μl of a solution made by adding together 43.5 ml of water, 6.5 ml of 70% perchloric acid ($HClO_4$) and 50 ml of 20 N sulfuric acid ($H_2SO_4$) is added. This is heated at 95° C. for 2 hours in a tube with a marble on top of it. The mixture is then placed in an oven at 165° C. and heated for an additional 2 hours, then cooled to room temperature. Next, one ml of reagent 5, made by the following method, is added to the sample:

Reagent 1: 1.36 grams of sodium acetate $0.3H_2O$ dissolved in 10 ml water.

Reagent 2: 500 mg ammonium molybdate dissolved in 20 ml water.

Reagent 3: 2 ml of reagent 1, 2 ml of reagent 2 and 16 ml of water.

Reagent 4: 2 gm ascorbic acid dissolved in 20 ml water, prepared immediately prior to use.

Reagent 5: Add in an ice bath 9 ml of reagent 3 and 1 ml of reagent 4.

After adding reagent 5 the tubes are mixed thoroughly and the optical density read at 820 nanometers in a spectrophotometer. A standard curve consisting of sodium phosphate monobasic (range of 0.1-5 μg per tube) is used to calculate the amount of phosphate present in the test samples. (Lowry, O. H., N. R. Roberts, K. Y. Leiner, M. L. Wu and A. L. Farr., (1954), *Biol. Chem.* 207, 1.)

The compositions of the invention are useful in a variety of different applications including in vitro, in situ and in vivo diagnosis of pathological status, such as infection. The compositions may be used to immunize subjects in vivo to prevent or treat infection. The compositions may also be used to develop antibodies and other binding peptides which are useful for the same purposes as the dPNAG compositions of the invention. Thus, the invention includes pharmaceutical compositions comprising dPNAG or corresponding binding agents (e.g., antibodies) that can be used for vaccination purposes to induce either active or passive immunity in a subject in need thereof. The invention also provides methods for generating binding agents, such as antibodies that bind to dPNAG, which can be used in the diagnosis and treatment of Staphylococcal infections and associated conditions.

dPNAG may be used in a conjugated or an unconjugated form. In a conjugated form, dPNAG may be conjugated to a carrier compound, either directly or via a linker. The conjugation can occur at any position in the glucosamine monomer unit or at the ends of the polymer.

A "carrier compound" as used herein is a compound that can be conjugated to a polysaccharide either directly or through the use of a linker and that may be immunologically active or inert.

Carrier compounds include but are not limited to proteins, or peptides, polysaccharides, nucleic acids, or other polymers, lipids, and small molecules. Proteins include for example, plasma proteins such as serum albumin, immunoglobulins, apolipoproteins and transferrin; bacterial polypeptides such as TRPLE, β-galactosidase, polypeptides such as herpes gD protein, allergens, diphtheria and tetanus toxoids, *salmonella* flagellin, hemophilus pilin, hemophilus 15 kDa, 28-30 kDa and 40 kDa membrane proteins, *Escherichia coli*, heat label enterotoxin ltb, cholera toxin, and viral proteins including rotavirus VP and respiratory syncytial virus f and g proteins. The proteins useful in the invention include any protein that is safe for administration to mammals and optionally that is an immunologically effective carrier protein.

Carrier compounds that are useful particularly for immunization include proteins such as keyhole limpet hemocyanin, serum albumin, bovine thyroglobulin, or soy bean trypsin inhibitor. Any other compound that is immunogenic in the species of animal to be immunized can similarly be used.

Many methods are known in the art for conjugating a polysaccharide to a protein. In general, the polysaccharide should be activated or otherwise rendered amenable to conjugation, i.e., at least one moiety must be rendered capable of covalently bonding to a protein or other molecule. Many such methods are known in the art. For instance, U.S. Pat. No. 4,356,170, issued to Jennings, describes the use of periodic acid to generate aldehyde groups on the polysaccharide and then performs reductive amination using cyanoborohydride. U.S. Pat. No. 4,663,160, issued to Tsay et al., also used periodic acid to generate aldehyde groups but then linked the polysaccharide to a protein derivatized with a 4-12 carbon moiety (prepared in the presence of a condensing agent) with a Schiff's base reaction in the presence of a reducing agent such as cyanoborohydride. U.S. Pat. No. 4,619,828, issued to Gordon, used cyanogen bromide to active the polysaccharide and then conjugated it through a spacer bridge of 4-8 carbon atoms to the protein. In U.S. Pat. No. 4,808,700, issued to Anderson and Clements, a polysaccharide was modified to produce at least one reducing end using limited oxidative cleavage by periodate, hydrolysis by glycosidases, or acid hydrolysis and was conjugated to a protein through reductive amination in the presence of cyanoborohydride. U.S. Pat. No. 4,711,779, issued to Porro and Costantino, described the activation of polysaccharides by introducing primary amino groups into the terminal reducing group using sodium cyanoborohydride, followed by conversion to esters in the presence of adipic acid derivatives and conjugation to a toxoid in the presence of an organic solvent, such as dimethylsulfoxide. Many other methods of conjugation are known in the art.

The carrier compound may be conjugated to dPNAG through a linker or spacer. A polysaccharide may be coupled to a linker or a spacer by any means known in the art including, for example using a free reducing end of the polysaccharide to produce a covalent bond with a spacer or linker. A covalent bond may be produced by converting a free reducing end of dPNAG into a free 1-aminoglycocide, that can subsequently be covalently linked to a spacer by acylation. (Lundquist et al., *J. Carbohydrate Chem.*, 10:377 (1991)). Alternatively, dPNAG may be covalently linked to the spacer using an N-hydroxysuccinimide active ester as activated group on the spacer. (Kochetkow, *Carbohydrate Research*, 146:C1 (1986)). The free reducing end of dPNAG may also be converted to a lactone using iodine and potassium hydroxide. (Isebell et al., *Methods of Carbohydrate Chemistry, Academic Press*, New York (1962)). The lactone can be covalently linked to the spacer by means of a primary amino group on the spacer or linker. The free reducing end of dPNAG may also be covalently linked to the linker or spacer using reductive amination.

The invention embraces antibodies that bind to dPNAG. The antibodies may be either monoclonal antibodies or polyclonal antibodies. The dPNAG antibodies bind to dPNAG and may also bind to forms of PNAG that are greater than 50% acetylated.

Polyclonal antibodies generally are raised in animals by multiple subcutaneous or intraperitoneal injections of an antigen and an adjuvant. Polyclonal antibodies to dPNAG can be generated by injecting dPNAG in conjugated or unconjugated form, alone or in combination with an adjuvant.

An example of polyclonal antibody preparation follows. dPNAG or a dPNAG conjugate is combined with an adjuvant such as Freund's complete adjuvant (e.g., 100 μg of conjugate for rabbits or mice in 1-3 volumes of Freund's) and injected intradermally at multiple sites. Approximately one month later, the animals are boosted with ⅕-1/10 of the original amount of antigen, or antigen conjugate, in adjuvant by subcutaneous injection at multiple sites. One to two weeks later the animals are bled, and the serum is assayed for the presence of antibody. The animals may be repeatedly boosted until the antibody titer plateaus. The animal may be boosted with dPNAG alone, dPNAG conjugate, or dPNAG conjugated to a different carrier compound, with or without an adjuvant. In some embodiments, the boosts may comprise PNAG rather than dPNAG, or they may contain a mixture of dPNAG and PNAG.

In addition to supplying a source of polyclonal antibodies, the immunized animals can be used to generate anti-dPNAG monoclonal antibodies. As used herein, the term "monoclonal antibody" refers to a homogenous population of immunoglobulins that bind to the same epitope (i.e., antigenic determinant) of dPNAG. This epitope may also be present in PNAG forms that are greater than 50% acetylated. Monoclonal antibodies have the same Ig gene rearrangement and thus demonstrate identical binding specificity. Monoclonal antibodies can be prepared by any method known in the art such as by immortalizing spleen cells isolated from the immunized animal by e.g., fusion with myeloma cells or by Epstein Barr Virus transformation, and screening for clones expressing the desired antibody. Other methods involve isolation of rearranged Ig gene sequences and cloning into immortalized cell lines. Methods for preparing and using monoclonal antibodies are well known in the art.

Murine anti-dPNAG monoclonal antibodies may be made by any of these methods utilizing dPNAG as an immunogen. The following description of a method for developing an anti-dPNAG monoclonal antibody is exemplary and is provided for illustrative purposes only. Balb/c mice are immunized intraperitoneally with approximately 75-100 μg of purified dPNAG in complete Freund's adjuvant. Booster injections of approximately 25-50 μg dPNAG in incomplete Freund's are administered on approximately days 15 and 35 after the initial injection. On day 60-65, the mice receive booster injections of approximately 25 μg dPNAG in the absence of adjuvant. Booster injection may alternatively comprise a native PNAG preparation or a mixture of dPNAG and PNAG. Three days later, the mice are killed and the isolated spleen cells fused to murine myeloma NS-1 cells using polyethylene glycol by a procedure such as that described by Oi (Oi VT: Immunoglobulin-producing hybrid cell lines in *Herzenberg* LA (ed): Selected Methods in Cellular Biology, San Francisco, Calif., Freeman, (1980)). Hybridoma cells are selected using hypoxanthine, aminopterin, and thymidine (HAT) and grown in culture. Fourteen to fifteen days after fusion, hybridoma cells producing anti-dPNAG monoclonal antibodies are identified using a solid-phase radioimmunoas say by capturing anti-dPNAG antibodies from conditioned media with immobilized goat anti-mouse IgG followed by quantitation of specifically bound $^{125}$I-labeled dPNAG or PNAG. Hybridomas testing positive for antibodies against dPNAG are subcloned by limiting dilution and re-tested. Ascites for the hybridomas is then prepared in pristane-primed BALB/c mice by injecting approximately $1 \times 10^6$ cells/mouse. Concentrates enriched in the selected monoclonal antibodies are produced from ascites fluid by gel filtration on S-200 and concentrated with $NH_4SO_4$. The pellets are dissolved in an appropriate storage solution such as 50% glycerol/$H_2O$ and are stored at 4° C.

An "anti-dPNAG antibody" as used herein includes humanized antibodies and antibody fragments as well as intact monoclonal and polyclonal antibodies that bind to dPNAG and in some instances to PNAG forms that are greater than 50% acetylated also. A "humanized monoclonal antibody" as used herein is a human monoclonal antibody or functionally active fragment thereof having at least human constant regions and a dPNAG binding region (e.g., a CDR) from a mammal of a species other than a human. An intact humanized anti-dPNAG monoclonal antibody in an isolated form or in a pharmaceutical preparation is particularly suited to some aspects of the invention. Humanized antibodies have particular clinical utility in that they specifically recognize dPNAG and preferably native PNAG forms also, but will not evoke an immune response in humans against the antibody itself. In one preferred embodiment, a murine CDR is grafted into the framework region of a human antibody to prepare the "humanized antibody." See, e.g., L. Riechmann et al., Nature 332, 323 (1988); M. S. Neuberger et al., Nature 314, 268 (1985) and EPA 0 239 400 (published Sep. 30, 1987).

Human monoclonal antibodies may be made by any of the methods known in the art, such as those disclosed in U.S. Pat. No. 5,567,610, issued to Borrebaeck et al., U.S. Pat. No. 565,354, issued to Ostberg, U.S. Pat. No. 5,571,893, issued to Baker et al, Kozber, *J. Immunol.* 133: 3001 (1984), Brodeur, et al., *Monoclonal Antibody Production Techniques and Applications*, p. 51-63 (Marcel Dekker, Inc, new York, 1987), and Boerner et al., *J. Immunol.*, 147: 86-95 (1991). In addition to the conventional methods for preparing human monoclonal antibodies, such antibodies may also be prepared by immunizing transgenic animals that are capable of producing human antibodies (e.g., Jakobovits et al., *PNAS USA*, 90: 2551 (1993), Jakobovits et al., *Nature*, 362: 255-258 (1993), Bruggermann et al., *Year in Immunol.*, 7:33 (1993) and U.S. Pat. No. 5,569,825 issued to Lonberg).

The following examples of methods for preparing humanized monoclonal antibodies that interact with dPNAG and preferably other native PNAG forms also, are exemplary and are provided for illustrative purposes only. Humanized monoclonal antibodies, for example, may be constructed by replacing the non-CDR regions of a non-human mammalian antibody with similar regions of human antibodies while retaining the epitopic specificity of the original antibody. For example, non-human CDRs and optionally some of the framework regions may be covalently joined to human FR and/or Fc/pFc' regions to produce a functional antibody. There are entities in the United States which will synthesize humanized antibodies from specific murine antibody regions commercially, such as Protein Design Labs (Mountain View Calif.), Abgenix, and Medarex.

European Patent Application 0239400, the entire contents of which is hereby incorporated by reference, provides an exemplary teaching of the production and use of humanized monoclonal antibodies in which at least the CDR portion of a murine (or other non-human mammal) antibody is included in the humanized antibody. Briefly, the following methods are useful for constructing a humanized CDR monoclonal antibody including at least a portion of a mouse CDR. A first replicable expression vector including a suitable promoter operably linked to a DNA sequence encoding at least a variable domain of an Ig heavy or light chain and the variable domain comprising framework regions from a human antibody and a CDR region of a murine antibody is prepared. Optionally a second replicable expression vector is prepared which includes a suitable promoter operably linked to a DNA sequence encoding at least the variable domain of a complementary human Ig light or heavy chain respectively. A cell line is then transformed with the vectors. Preferably the cell line is an immortalized mammalian cell line of lymphoid origin, such as a myeloma, hybridoma, trioma, or quadroma cell line, or is a normal lymphoid cell which has been immortalized by transformation with a virus. The transformed cell line is then cultured under conditions known to those of skill in the art to produce the humanized antibody.

As set forth in European Patent Application 0239400 several techniques are well known in the art for creating the particular antibody domains to be inserted into the replicable vector. (Preferred vectors and recombinant techniques are discussed in greater detail below.) For example, the DNA sequence encoding the domain may be prepared by oligonucleotide synthesis. Alternatively a synthetic gene lacking the CDR regions in which four framework regions are fused together with suitable restriction sites at the junctions, such that double stranded synthetic or restricted subcloned CDR cassettes with sticky ends could be ligated at the junctions of the framework regions. Another method involves the preparation of the DNA sequence encoding the variable CDR containing domain by oligonucleotide site-directed mutagenesis. Each of these methods is well known in the art. Therefore, those skilled in the art may construct humanized antibodies containing a murine CDR region without destroying the specificity of the antibody for its epitope.

Human antibodies may also be obtained by recovering antibody-producing lymphocytes from the blood or other tissues of humans producing antibody to dPNAG. These lymphocytes can be treated to produce cells that grow on their own in the laboratory under appropriate culture conditions. The cell cultures can be screened for production of antibody to dPNAG and then cloned. Clonal cultures can be used to produce human monoclonal antibodies to dPNAG, or the genetic elements encoding the variable portions of the heavy and light chain of the antibody can be cloned and inserted into nucleic acid vectors for production of antibody of different types.

dPNAG binding antibody fragments are also encompassed by the invention. As is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions of the antibody, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. An isolated F(ab')$_2$ fragment is referred to as a bivalent monoclonal fragment because of its two antigen binding sites. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd (heavy chain variable region). The Fd fragments are the major determinant of antibody specificity (a single Fd fragment may be associated with up to ten different light chains without altering antibody specificity) and Fd fragments retain epitope-binding ability in isolation.

The terms Fab, Fc, pFc', F(ab')$_2$ and Fv are employed with either standard immunological meanings [Klein, *Immunology* (John Wiley, New York, N.Y., 1982); Clark, W. R. (1986) *The Experimental Foundations of Modern Immunology* (Wiley & Sons, Inc., New York); Roitt, I. (1991) *Essential Immunology*, 7th Ed., (Blackwell Scientific Publications, Oxford)]. Well-known functionally active antibody fragments include but are not limited to F(ab')$_2$, Fab, Fv and Fd fragments of antibodies. These fragments which lack the Fc fragment of intact antibody, clear more rapidly from the circulation, and may have less non-specific tissue binding than an intact antibody (Wahl et al., *J. Nucl. Med.* 24:316-325 (1983)). For example, single-chain antibodies can be constructed in accordance with the methods described in U.S. Pat. No. 4,946,778 to Ladner et al. Such single-chain antibodies include the variable regions of the light and heavy chains joined by a flexible linker moiety. Methods for obtaining a single domain antibody ("Fd") which comprises an isolated variable heavy chain single domain, also have been reported (see, for example, Ward et al., *Nature* 341:644-646 (1989), disclosing a method of screening to identify an antibody heavy chain variable region (V$_H$ single domain antibody) with sufficient affinity for its target epitope to bind thereto in isolated form). Methods for making recombinant Fv fragments based on known antibody heavy chain and light chain variable region sequences are known in the art and have been described, e.g., Moore et al., U.S. Pat. No. 4,462,334. Other references describing the use and generation of antibody fragments include e.g., Fab fragments (Tijssen, Practice and Theory of Enzyme Immunoassays (Elsevieer, Amsterdam, 1985)), Fv fragments (Hochman et al., Biochemistry 12: 1130 (1973); Sharon et al., Biochemistry 15: 1591 (1976); Ehrlch et al., U.S. Pat. No. 4,355,023) and portions of antibody molecules (Audilore-Hargreaves, U.S. Pat. No. 4,470,925). Thus, those skilled in the art may construct antibody fragments from various portions of intact antibodies without destroying the specificity of the antibodies for the dPNAG epitope. It is to be understood that the epitope recognized by anti-dPNAG antibodies may also be present on other native PNAG forms.

The antibody fragments also encompass "humanized antibody fragments." As one skilled in the art will recognize, such fragments could be prepared by traditional enzymatic cleavage of intact humanized antibodies. If, however, intact antibodies are not susceptible to such cleavage, because of the nature of the construction involved, the noted constructions can be prepared with immunoglobulin fragments used as the starting materials or, if recombinant techniques are used, the DNA sequences, themselves, can be tailored to encode the desired "fragment" which, when expressed, can be combined in vivo or in vitro, by chemical or biological means, to prepare the final desired intact immunoglobulin fragment.

Other dPNAG binding agents having binding specificity for dPNAG can be used in the diagnostic methods of the invention. Several routine assays may be used to easily identify dPNAG binding peptides. Screening assays for identifying peptides of the invention are performed for example, using phage display procedures such as those described in Hart, et al., *J. Biol. Chem.* 269:12468 (1994). Hart et al. report a filamentous phage display library for identifying novel peptide ligands for mammalian cell receptors. In general, phage display libraries using, e.g., M13 or fd phage, are prepared using conventional procedures such as those described in the foregoing reference. The libraries display inserts containing from 4 to 80 amino acid residues. The inserts optionally represent a completely degenerate or a biased array of peptides. Ligands that bind selectively to dPNAG are obtained by selecting phage that express on their surface a ligand that binds to dPNAG. These phage then are subjected to several cycles of reselection to identify the peptide ligand-expressing phage that have the most useful binding characteristics. Typically, phage that exhibit the best binding characteristics (e.g., highest affinity) are further characterized by nucleic acid analysis to identify the particular amino acid sequences of the peptides expressed on the phage surface and the optimum length of the expressed peptide to achieve optimum binding to dPNAG.

Alternatively, such peptide ligands can be selected from combinatorial libraries of peptides containing one or more amino acids. Such libraries can further be synthesized which contain non-peptide synthetic moieties which are less subject to enzymatic degradation compared to their naturally-occurring counterparts.

To determine whether a peptide binds to dPNAG any known binding assay may be employed. For example, the peptide may be immobilized on a surface and then contacted with a labeled dPNAG. The amount of dPNAG which interacts with the peptide or the amount which does not bind to the peptide may then be quantitated to determine whether the peptide binds to dPNAG. A surface having an anti-dPNAG antibody immobilized thereto may serve as a positive control. Binding assays may also determine the extent to which a putative dPNAG specific antibody binds to other native forms of PNAG.

The compositions of the invention are useful for many in vivo, and in vitro purposes. For example, the compositions of the invention are useful for producing an antibody response, e.g., as a vaccine for active immunization of humans and animals to prevent Staphylococcal infection and infections caused by other species of bacteria that make PNAG; as a vaccine for immunization of humans or animals to produce anti-dPNAG antibodies that can be administered to other humans or animals to prevent or treat Staphylococcal infections; as an antigen to screen for biological agents such as monoclonal antibodies capable of preventing Staphylococcal infection, libraries of genes involved in making antibodies, or peptide mimetics; as a diagnostic reagent for Staphylococcal infections and infections caused by other species of bacteria that make PNAG; and as a diagnostic reagent for determining the immunologic status of humans or animals in regard to their susceptibility to Staphylococcal infections and infections caused by other species of bacteria that make PNAG.

dPNAG can be used to protect a subject against infection with bacteria that make PNAG by inducing active immunity to infection by Staphylococci in a subject. The method is accomplished by administering to the subject an effective amount for inducing an immune response such as an antibody response against Staphylococci of any of the dPNAG compositions of the invention. "Active immunity" as used herein involves the introduction of an antigen into a subject such that the antigen causes differentiation of some lymphoid cells into cells that produce antibody and in certain instances other lymphoid cells into memory cells. The memory cells do not secrete antibodies but rather incorporate the antibodies into their membrane in order to sense antigen if it is administered to the body again.

The method is useful for inducing immunity to infection by Staphylococci. "Staphylococci" as used herein refers to all Staphylococcal bacterial species expressing the PNAG. Although not intending to be bound by any particular mechanism, it is thought that the highly acetylated forms of PNAG (i.e., >50% acetylated) are not able to elicit production of opsonic, protective antibodies, to the same extent as dPNAG. Bacteria that are classified as Staphylococci are well known to those of skill in the art and are described in the microbiology literature. Staphylococci expressing PNAG include but are not limited *Staphylococcus epidermidis* (including RP62A (ATCC Number 35984), RP12 (ATCC Number 35983), and M187), *Staphylococcus aureus* (including RN4220 (pCN27) and MN8 mucoid), and strains such as *Staphylococcus carnosus* transformed with the genes in the ica locus (including TM300 (pCN27)). Other bacterial strains expressing PNAG can be identified easily by those of ordinary skill in the art. For instance, Staphylococcal bacteria that express the ica locus will express PNAG. One of ordinary skill in the art can easily screen for the expression of mRNA or protein related to the ica locus since the nucleic acid sequence of the ica locus is known (SEQ ID NO:1 and originally described in Heilmann, C., O. Schweitzer, C. Gerke, N. Vanittanakom, D. Mack and F. Gotz (1996) Molecular basis of intercellular adhesion in the biofilm-forming *Staphylococcus epidermidis*. *Molec. Microbiol.* 20:1083.) Bacterial strains expressing PNAG also can be identified by immunoelectron microscopy (or other immunoassay) using anti-PNAG antibodies or anti-dPNAG antibodies to detect the presence of PNAG on the surface of the bacteria. Additionally the capsule of bacterial strains can be isolated and analyzed using liquid chromatography and mass spectroscopy.

A "subject" as used herein is a warm-blooded mammal and includes, for instance, humans, primates, horses, cows, swine, goats, sheep, dogs, and cats. In some embodiments, the subject is a non-rodent subject. A non-rodent subject is any subject as defined above, but specifically excluding rodents such as mice, rats, and rabbits. In some embodiments, the preferred subject is a human.

dPNAG may be administered to any subject capable of inducing an immune response such as an antibody response to an antigen. The antigen is especially suited to induce active immunization against systemic infection caused by Staphylococci in a subject capable of producing an immune response and at risk of developing a Staphylococcal infection. A subject capable of producing an immune response and at risk of developing a Staphylococcal infection is a mammal possessing an immune system that is at risk of being exposed to environmental Staphylococci. For instance, hospitalized patients are at risk of developing Staphylococcal infection as a result of exposure to the bacteria in the hospital environment. Particular high risk populations for developing infection by *S. aureus* include, for example, renal disease patients on dialysis, and individuals undergoing high risk surgery. High risk populations for developing infection by *S. epidermidis* also include, for example, patients with indwelling medical devices, such as intravenous lines (e.g., central lines), or prostheses (e.g., hip or knee replacement prostheses), because clinical isolates are often highly adherent to plastic surfaces due to their extracellular material (referred to as biofilm or slime). In some embodiments, the subject is a subject that has received a medical device implant and in other embodiments, the subject is one that has not received a medical device implant but may be scheduled to receive one. Subjects at a high risk of developing infection by *S. epidermidis* further include, for example, pre-term neonates and patients undergoing chemotherapy.

dPNAG can be administered to the subject in an effective amount for inducing an antibody response. An "effective amount for inducing an immune response (e.g., an antibody response)" as used herein is an amount of dPNAG which is sufficient to (i) assist the subject in producing its own immune protection by e.g. inducing the production of anti-dPNAG antibodies in the subject (that may recognize both dPNAG and highly acetylated forms of PNAG), inducing the production of memory cells, and possibly a cytotoxic lymphocyte reaction etc. and/or (ii) prevent infection by Staphylococci from occurring in a subject which is exposed to Staphylococci.

In some preferred embodiments, the effective amount of a dPNAG vaccine for stimulating an immune response is an amount of dPNAG vaccine that is capable of eliciting the production of antibodies that are cross-reactive with at least two species of *Staphylococcus*, e.g., *S. aureus* and *S. epidermidis*.

One of ordinary skill in the art can assess whether an amount of dPNAG is sufficient to induce active immunity by routine methods known in the art. For instance, the ability of a specific antigen to produce antibody in a mammal can be assessed by screening for antibodies in a mouse or other subject using the dPNAG antigen.

The anti-dPNAG antibodies of the invention are useful for inducing passive immunization in a subject by preventing the development of systemic infection in those subjects at risk of exposure to infectious agents. The method for inducing passive immunity to infection by Staphylococci such as *Staphylococcus aureus* is performed by administering to a subject an effective amount of an anti-dPNAG antibody for inducing an immune response to Staphylococci e.g., by causing opsonization of Staphylococci such as *Staphylococcus aureus*. "Passive immunity" as used herein involves the administration of antibodies to a subject, wherein the antibodies are produced in a different subject (including subjects of the same and different species), such that the antibodies attach to the surface of the bacteria and cause the bacteria to be phagocytosed.

The anti-dPNAG antibody may be administered to any subject at risk of developing a Staphylococcal infection to induce passive immunity, and in some embodiments may be particularly suited for subjects incapable of inducing active immunity to dPNAG. Since vaccination with dPNAG might not be completely effective in high risk immunocompromised subjects, these subjects will benefit from treatment with antibody preparations raised against Staphylococci such as *Staphylococcus aureus*. A subject that is incapable of inducing an immune response is an immunocompromised subject (e.g. patient undergoing chemotherapy, AIDS patient, etc.) or a subject that has not yet developed an immune system (e.g. pre-term neonate).

The anti-dPNAG antibody may be administered to a subject at risk of developing a Staphylococcal infection to prevent the infectious agent from multiplying in the body or to kill the infectious agent. The anti-PNAG antibody may also be administered to a subject who already has an infection caused by Staphylococci to prevent the infectious agent from multiplying in the body or to kill the infectious agent.

The anti-dPNAG antibody of the invention is administered to the subject in an effective amount for inducing an immune response to Staphylococci such as *Staphylococcus aureus*. An "effective amount for inducing an immune response to Staphylococci" as used herein is an amount of anti-dPNAG antibody that is sufficient to (i) prevent infection by Staphylococci from occurring in a subject which is exposed to Staphylococci; (ii) inhibit the development of infection, i.e., arresting or slowing its development; and/or (iii) relieve the infection, i.e., eradication of the bacteria in infected subjects.

Using routine procedures known to those of ordinary skill in the art, one can determine whether an amount of anti-dPNAG antibody is an "effective amount for inducing an immune response to Staphylococci" in an in vitro opsonization assay which is predictive of the degree of opsonization of an antibody. An antibody that opsonizes a Staphylococcal bacteria is one that when added to a sample of Staphylococcal bacteria causes phagocytosis of the bacteria. An opsonization assay may be a colorimetric assay, a chemiluminescent assay, a fluorescent or radiolabel uptake assay, a cell mediated bactericidal assay or other assay which measures the opsonic potential of a material. The following opsonization assay may be used to determine an effective amount of anti-dPNAG antibody. Anti-dPNAG antibody is incubated with an Staphylococcal bacteria and a eukaryotic phagocytic cell and optionally complement proteins. The opsonic ability of the anti-PNAG antibody is determined based on the amount of Staphylococci that remain after incubation. This can be accomplished by comparing the number of surviving Staphylococci between two similar assays, only one of which includes opsonizing immunoglobulin. A reduction in the number of Staphylococci, as compared to incubation with control non-specific immunoglobulin, indicates opsonization.

The methods of the invention are also useful for inducing passive immunization to Staphylococci in a subject by administering to a subject an effective amount for inducing opsonization of Staphylococci of an anti-dPNAG$_{pure}$ antibody. An anti-dPNAG$_{pure}$ antibody as used herein is an antibody which specifically interacts with a pure dPNAG antigen of the invention and induces opsonization of coagulase-negative or coagulase-positive Staphylococci but that may not interact with an impure preparation of dPNAG. As discussed above, impure dPNAG preparations may be contaminated with teichoic acid or other impurities that can interfere with the immunogenicity of the antigen. One of ordinary skill in the art can easily identify whether an anti-dPNAG antibody is an anti-dPNAG$_{pure}$ antibody by using routine binding assays. For instance, an anti-dPNAG antibody may be immobilized on a surface and then contacted with a labeled impure dPNAG preparation or a labeled pure dPNAG preparation. The amount of dPNAG preparation (pure vs. impure preparation) which interacts with the antibody or the amount which does not bind to the antibody may then be quantitated to determine whether the antibody binds to an impure dPNAG preparation. In important embodiments, the anti-dPNAG$_{pure}$ antibody is effective against coagulase-negative and coagulase-positive Staphylococci or against any appropriate microbial organism expressing dPNAG or highly acetylated PNAG on its surface.

dPNAG antigen may be formulated as a vaccine. A suitable carrier media for formulating a vaccine includes sodium phosphate-buffered saline (pH 7.4) or 0.125 M aluminum phosphate gel suspended in sodium phosphate-buffered saline at pH 6 and other conventional media. Generally, vaccines contain from about 5 to about 100 µg, and preferably about 10-50 µg of the antigen to elicit effective levels of antibody in warm-blooded mammals. When administered as a vaccine the dPNAG can optionally include an adjuvant.

The term "adjuvant" is intended to include any substance which is incorporated into or administered simultaneously with dPNAG, which potentiates the immune response in the subject. Adjuvants include but are not limited to aluminum compounds, e.g., gels, aluminum hydroxide and aluminum phosphate, and Freund's complete or incomplete adjuvant (e.g., in which the dPNAG antigen is incorporated in the aqueous phase of a stabilized water in paraffin oil emulsion). The paraffin oil may be replaced with different types of oils, e.g., squalene or peanut oil. Other materials with adjuvant properties include BCG (attenuated *Mycobacterium tuberculosis*), calcium phosphate, levamisole, isoprinosine, polyanions (e.g., poly A:U), lentinan, pertussis toxin, lipid A, saponins, QS-21 and peptides, e.g. muramyl dipeptide. Rare earth salts, e.g., lanthanum and cerium, may also be used as adjuvants. The amount of adjuvants depends on the subject and the particular dPNAG antigen used (e.g., the level of acetate substitution) and can be readily determined by one skilled in the art without undue experimentation.

In general, when administered for therapeutic purposes, the formulations of the invention are applied in pharmaceutically acceptable solutions. Such preparations may routinely contain pharmaceutically acceptable concentrations of salt, buffering agents, preservatives, compatible carriers, adjuvants, and optionally other therapeutic ingredients.

The compositions of the invention may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulphuric, nitric, phosphoric, maleic, acetic, salicyclic, p-toluene sulphonic, tartaric, citric, methane sulphonic, formic, malonic, succinic, naphthalene-2-sulphonic, and benzene sulphonic. Also, pharmaceutically acceptable salts can be prepared as alkaline metal or alkaline earth salts, such as sodium, potassium or calcium salts of the carboxylic acid group.

Suitable buffering agents include: acetic acid and a salt (1-2% W/V); citric acid and a salt (1-3% W/V); boric acid and a salt (0.5-2.5% W/V); and phosphoric acid and a salt (0.8-2% W/V). Suitable preservatives include benzalkonium chloride (0.003-0.03% W/V); chlorobutanol (0.3-0.9% W/V); parabens (0.01-0.25% W/V) and thimerosal (0.004-0.02% W/V).

The present invention provides pharmaceutical compositions, for medical use, that comprise dPNAG together with one or more pharmaceutically acceptable carriers and optionally other therapeutic ingredients. The term "pharmaceutically-acceptable carrier" as used herein, and described more fully below, means one or more compatible solid or liquid filler, diluents or encapsulating substances which are suitable for administration to a human or other animal. In the present invention, the term "carrier" denotes an organic or inorganic ingredient, natural or synthetic, with which the active ingredient is combined to facilitate the application. The components of the pharmaceutical compositions also are capable of being commingled with dPNAG, and with each other, in a manner such that there is no interaction which would substantially impair the desired pharmaceutical efficiency.

Compositions suitable for parenteral administration conveniently comprise a sterile aqueous preparation of the polysaccharide, which can be isotonic with the blood of the recipient. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono or di-glycerides. In addition, fatty acids such as oleic acid find use in the preparation of injectables. Carrier formulations suitable for subcutaneous, intramuscular, intraperitoneal, intravenous, etc. administrations may be found in Remington's Pharmaceutical Sciences, Mack Publishing Company, Easton, Pa.

The preparations of the invention are administered in effective amounts. An effective amount, as discussed above, is that amount of dPNAG or anti-dPNAG antibody that will alone, or together with further doses, induce active immunity or opsonization of the infectious bacteria, respectively. It is believed that doses ranging from 1 nanogram/kilogram to 100 milligrams/kilogram, depending upon the mode of administration, will be effective. The preferred range is believed to be between 500 nanograms and 500 micrograms/kilogram, and most preferably between 1 microgram and 100 micrograms/kilogram. The absolute amount will depend upon a variety of factors including whether the administration is performed on a high risk subject not yet infected with the bacteria or on a subject already having an infection, the concurrent treatment, the number of doses and the individual patient parameters including age, physical condition, size and weight. These are factors well known to those of ordinary skill in the art and can be addressed with no more than routine experimentation. It is preferred generally that a maximum dose be used, that is, the highest safe dose according to sound medical judgment.

Multiple doses of the pharmaceutical compositions of the invention are contemplated. Generally immunization schemes involve the administration of a high dose of an antigen followed by subsequent lower doses of antigen after a waiting period of several weeks. Further doses may be administered as well. The dosage schedule for passive immunization would be quite different with more frequent administration if necessary. Any regimen that results in an enhanced immune response to bacterial infection and/or subsequent protection from infection may be used. Desired time intervals for delivery of multiple doses of a particular dPNAG can be determined by one of ordinary skill in the art employing no more than routine experimentation.

A variety of administration routes are available. The particular mode selected will depend, of course, upon the particular dPNAG selected, the particular condition being treated and the dosage required for therapeutic efficacy. The methods of this invention, generally speaking, may be practiced using any mode of administration that is medically acceptable, meaning any mode that produces effective levels of an immune response without causing clinically unacceptable adverse effects. Preferred modes of administration are parenteral routes. The term "parenteral" includes subcutaneous, intravenous, intramuscular, intraperitoneal, and intrasternal injection, or infusion techniques. Other routes include but are not limited to oral, nasal, dermal, sublingual, and local.

The compositions may conveniently be presented in unit dosage form and may be prepared by any of the methods well known in the art of pharmacy. All methods include the step of bringing dPNAG or a dPNAG binding agent into association with a carrier which constitutes one or more accessory ingredients. In general, the compositions are prepared by uniformly and intimately bringing the polymer into association with a liquid carrier, a finely divided solid carrier, or both, and then, if necessary, shaping the product. The polymer may be stored lyophilized.

Other delivery systems can include time-release, delayed release or sustained release delivery systems. Such systems can avoid repeated administrations of the polysaccharides of the invention, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. No. 4,452,775 (Kent); U.S. Pat. No. 4,667,014 (Nestor et al.); and U.S. Pat. Nos. 4,748,034 and 5,239,660 (Leonard) and (b) diffusional systems in which an active component permeates at a controlled rate through a polymer, found in U.S. Pat. No. 3,832,253 (Higuchi et al.) and U.S. Pat. No. 3,854,480 (Zaffaroni). In addition, a pump-based hardware delivery system can be used, some of which are adapted for implantation.

It will also be appreciated by those of ordinary skill in the art that the PNAG antigens of the present invention may have adjuvant properties by themselves. To the extent that the polysaccharides described herein potentiate human immune responses, they can be used as adjuvants in combination with other materials.

The dPNAG antigens and anti-dPNAG antibodies of the invention may be delivered in conjunction with another anti-bacterial (i.e., bactericidal) drug or in the form of anti-bacterial cocktails or with other bacterial antigens or anti-bacterial antibodies. An anti-bacterial antibiotic cocktail is a mixture of any of the compositions of the invention with an anti-bacterial drug. The use of antibiotics in the treatment of bacterial infection is routine. The use of antigens for inducing active immunization and antibodies to induce passive immunization is also routine. In this embodiment, a common administration vehicle (e.g., tablet, implant, injectable solution, etc.) could contain both the composition useful in this invention and the anti-bacterial antibiotic drug and/or antigen or antibody. Alternatively, the anti-bacterial antibiotic drug and/or antigen or antibody can be separately dosed. The anti-bacterial agent (e.g., an antibiotic) can also be conjugated to dPNAG or to an anti-dPNAG antibody.

Anti-bacterial antibiotic drugs are well known and include: penicillin G, penicillin V, ampicillin, amoxicillin, bacampicillin, cyclacillin, epicillin, hetacillin, pivampicillin, methicillin, nafcillin, oxacillin, cloxacillin, dicloxacillin, flucloxacillin, carbenicillin, ticarcillin, avlocillin, mezlocillin, piperacillin, amdinocillin, cephalexin, cephradine, cefadoxil, cefaclor, cefazolin, cefuroxime axetil, cefamandole, cefonicid, cefoxitin, cefotaxime, ceftizoxime, cefmenoxine, ceftriaxone, moxalactam, cefotetan, cefoperazone, ceftazidme, imipenem, clavulanate, timentin, sulbactam, neomycin, erythromycin, metronidazole, chloramphenicol, clindamycin, lincomycin, vancomycin, trimethoprim-sulfamethoxazole, aminoglycosides, quinolones, tetracyclines and rifampin. (See Goodman and Gilman's, Pharmacological Basics of Therapeutics, 8th Ed., 1993, McGraw Hill Inc.)

Other polysaccharide antigens and antibodies are well known in the art. For instance, the following polysaccharide antigens and/or antibodies thereto can be administered in conjunction with the dPNAG antigen and/or antibody: *Salmonella typhi* capsule Vi antigen (Szu, S. C., X. Li, A. L. Stone and J. B. Robbins, Relation between structure and immunologic properties of the Vi capsular polysaccharide, *Infection and Immunity*. 59:4555-4561 (1991)); *E. Coli* K5 capsule (Vann, W., M. A. Schmidt, B. Jann and K. Jann, The structure of the capsular polysaccharide (K5 antigen) of urinary tract infective *Escherichia coli,* O10:K5:H4. A polymer similar to desulfo-heparin, *European Journal of Biochemistry*. 116: 359-364, (1981)); *Staphylococcus aureus* type 5 capsule (Fournier, J.-M., K. Hannon, M. Moreau, W. W. Karakawa and W. F. Vann, Isolation of type 5 capsular polysaccharide from *Staphylococcus aureus, Ann. Inst. Pasteur/Microbiol*. (Paris). 138: 561-567, (1987)); *Rhizobium melilori* expolysaccharide II (Glazebrook, J. and G. C. Walker, a novel expolysaccharide can function in place of the calcofluor-binding exopolysaccharide in nodulation of alfalfa by *Rhizobium meliloti, Cell*. 65:661-672 (1989)); Group B *streptococcus* type III (Wessels, M. R., V. Pozsgay, D. L. Kasper and H. J. Jennings, Structure and immunochemistry of an oligosaccharide repeating unit of the capsular polysaccharide of type III group B *Streptococcus, Journal of Biological Chemistry*. 262:8262-8267 (1987)); *Pseudomonas aeruginosa* Fisher 7 O-specific side-chain (Knirel, Y. A., N. A. Paramonov, E. V. Vinogradov, A. S. Shashkov, B. A. N. K. Kochetkov, E. S. Stanislaysky and E. V. Kholodkova, Somatic antigens of *Pseudomonas aeruginosa* The structure of O-specific polysaccharide chains of lipopolysaccharides of *P. aeruginosa* O3 (Lanyi), 025 (Wokatsch) and Fisher immunotypes 3 and 7, *European Journal of Biochemistry*. 167:549, (1987)); *Shigella sonnei* O-specific side chain (Kenne, L., B. Lindberg and K. Petersson, Structural studies of the O-specific side-chains of the *Shigella sonnei* phase I lipopolysaccharide, *Carbohydrate Research*. 78:119-126, (1980)); *S. pneumoniae* type I capsule (Lindberg, B., Lindqvist, B., Lonngren, J., Powell, D. A., Structural studies of the capsular polysaccharide from *Streptococcus pneumoniae* type 1, *Carbohydrate Research*. 78:111-117 (1980)); and *Streptococcus pneumoniae* group antigen (Jennings, H. J., C. Lugowski and N. M. Young, Structure of the complex polysaccharide C-substance from *Streptococcus pneumoniae* type 1, *Biochemistry*. 19:4712-4719 (1980)).

Other non-polypeptide antigens and antibodies thereto are well known to the those of skill in the art and can be used in conjunction with the dPNAG compositions of the invention.

The dPNAG antigens and antibodies are also useful in diagnostic assays for determining an immunologic status of a subject or sample or can be used as reagents in immunoassays. For instance, the antibodies may be used to detect the presence in a sample of a bacteria having PNAG on the surface. If the bacteria is present in the sample, then the antibodies may be used to treat the infected subject. The antibodies may also be used to screen bacteria for the presence of PNAG antigen and to isolate dPNAG or PNAG antigen and bacteria containing dPNAG or PNAG antigen from complex mixtures.

The above-described assays and any other assay known in the art can be accomplished by labeling the dPNAG or antibodies and/or immobilizing the dPNAG or antibodies on an insoluble matrix. The analytical and diagnostic methods for using dPNAG and/or its antibodies use at least one of the following reagents: labeled analyte analogue, immobilized analyte analogue, labeled binding partner, immobilized binding partner, and steric conjugates. The label used can be any detectable functionality that does not interfere with the binding of analyte and its binding partner. Numerous labels are known for such use in immunoassays.

For example, compounds that may be detected directly, such as fluorochrome, chemiluminescent, and radioactive labels, as well as compounds that can be detected through reaction or derivitization, such as enzymes. Examples of these types of labels include $^{32}P$, $^{14}C$, $^{125}I$, $^{3}H$, and $^{131}I$ radioisotopes, fluorophores such as rare earth chelates or fluorescein and its derivatives, rhodamine and its derivatives, dansyl, umbelliferone, luciferases such as firefly luciferase and bacterial luciferase (U.S. Pat. No. 4,737,456), luciferin, 2,3-dihydrophthalavinediones, horseradish peroxidase (HRP), alkaline phosphatase, β-galactosidase, glucoamylase, lysozyme, saccharide oxidases such as glucose oxidase, galactose oxidase, and glucose-6-phosphate dehydrogenase. Heterocyclic oxidases such as uricase and xanthine oxidase, coupled to an enzyme that uses hydrogen peroxide to oxidize a dye precursor such as HRP, lactoperoxidase, or microperoxidase, biotin avidin, spin labels, bacteriophage labels, and stable free radicals.

The labels can be conjugated to dPNAG or anti-dPNAG antibody by methods known to those of ordinary skill in the art. For example, U.S. Pat. Nos. 3,940,475 and 3,645,090 demonstrate conjugation of fluorophores and enzymes to antibodies. Other assays which reportedly are commonly used with antigen and antibody and which can be used according to the invention include competition and sandwich assays.

The invention includes a method of preparing dPNAG antigen by producing a PNAG expressing host cell, by introducing an ica locus into a cell, isolating PNAG antigen from such a cell, and de-acetylating the antigen to form dPNAG. A PNAG host cell can be prepared by transfecting transducing or transforming a cell with the nucleic acid encoding the ica gene (SEQ ID NO:1). The cell can be a eukaryotic or prokaryotic cell but preferably is a bacterial cell. The cell may be a Staphylococci that does not naturally express PNAG.

The ica nucleic acid, in one embodiment, is operably linked to a gene expression sequence which directs the expression of the ica nucleic acid within a eukaryotic or prokaryotic cell. The "gene expression sequence" is any regulatory nucleotide sequence, such as a promoter sequence or promoter-enhancer combination, which facilitates the efficient transcription and translation of the ica nucleic acid to which it is operably linked. The gene expression sequence may, for example, be a mammalian or viral promoter, such as a constitutive or inducible promoter. Constitutive mammalian promoters include, but are not limited to, the promoters for the following genes: hypoxanthine phosphoribosyl transferase (HPTR), adenosine deaminase, pyruvate kinase, and β-actin. Exemplary viral promoters which function constitutively in cells include, for example, promoters from the simian virus, papilloma virus, adenovirus, human immunodeficiency virus (HIV), Rous sarcoma virus, cytomegalovirus, the long terminal repeats (LTR) of moloney leukemia virus and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the gene expression sequence shall include, as necessary, 5' non-transcribing and 5' non-translating sequences involved with the initiation of transcription and translation, respectively. Such 5' non-transcribing sequences will include a promoter region which includes a promoter sequence for transcriptional control of the operably joined ica nucleic acid. The gene expression sequences optionally include enhancer sequences or upstream activator sequences as desired.

The ica nucleic acid sequence and the gene expression sequence are said to be "operably linked" when they are covalently linked in such a way as to place the transcription and/or translation of the ica coding sequence under the influence or control of the gene expression sequence. If it is desired that the ica sequence be translated into a functional protein, two DNA sequences are said to be operably linked if induction of a promoter in the 5' gene expression sequence results in the transcription of the ica sequence and if the nature of the linkage between the two DNA sequences does not (1) result in the introduction of a frame-shift mutation, (2) interfere with the ability of the promoter region to direct the transcription of the ica sequence, or (3) interfere with the ability of the corresponding RNA transcript to be translated into a protein. Thus, a gene expression sequence would be operably linked to a ica nucleic acid sequence if the gene expression sequence were capable of effecting transcription of that ica nucleic acid sequence such that the resulting transcript might be translated into the desired protein or polypeptide.

The ica nucleic acid of the invention can be delivered to the host cell alone or in association with a vector. In its broadest sense, a "vector" is any vehicle capable of facilitating: (1) delivery of a nucleic acid molecule containing the genes in the ica locus that encode proteins involved in PNAG synthesis or (2) uptake of a nucleic acid molecule containing the genes in the ica locus that encode proteins involved in PNAG synthesis by a target cell. Preferably, the vectors transport the ica molecule into the target cell with reduced degradation relative to the extent of degradation that would result in the absence of the vector. In general, the vectors useful in the invention are divided into two classes: biological vectors and chemical/physical vectors. Biological vectors are useful for delivery/uptake of ica nucleic acids to/by a target cell. Chemical/physical vectors are useful for delivery/uptake of ica nucleic acids or ica polypeptides to/by a target cell.

Biological vectors include, but are not limited to, plasmids, phagemids, viruses, other vehicles derived from viral or bacterial sources that have been manipulated by the insertion or incorporation of the nucleic acid sequences of the invention, and free nucleic acid fragments which can be attached to the nucleic acid sequences of the invention. Viral vectors are a preferred type of biological vector and include, but are not limited to, nucleic acid sequences from the following viruses: retroviruses, such as: Moloney murine leukemia virus; Harvey murine sarcoma virus; murine mammary tumor virus; Rous sarcoma virus; adenovirus; adeno-associated virus; SV40-type viruses; polyoma viruses; Epstein-Barr viruses; papilloma viruses; herpes viruses; vaccinia viruses; polio viruses; and RNA viruses such as any retrovirus. One can readily employ other vectors not named but known in the art.

Preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. In general, the retroviruses are replication-deficient (i.e., capable of directing synthesis of the desired proteins, but incapable of manufacturing an infectious particle). Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman Co., New York (1990) and Murry, E. J. Ed. "Methods in Molecular Biology," vol. 7, Humana Press, Inc., Cliffton, N.J. (1991).

Another preferred virus for certain applications is the adeno-associated virus, a double-stranded DNA virus. The adeno-associated virus can be engineered to be replication-deficient and is capable of infecting a wide range of cell types and species. It further has advantages, such as heat and lipid solvent stability; high transduction frequencies in cells of diverse lineages; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for at least 100 passages in the absence of selective pressure, implying that the adeno-associated virus genomic integration is a relatively stable event. The adeno-associated virus can also function in an extrachromosomal fashion.

In addition to the biological vectors, chemical/physical vectors may be used to deliver a ica molecule to a target cell and facilitate uptake thereby. As used herein, a "chemical/physical vector" refers to a natural or synthetic molecule, other than those derived from bacteriological or viral sources, capable of delivering the ica molecule to a cell.

A preferred chemical/physical vector of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vessels (LUV), which range in size from 0.2-4.0 µm can encapsulate large macromolecules. RNA, DNA, and intact virions can be encapsulated within the aqueous interior and be delivered to cells in a biologically active form (Fraley, et al., Trends Biochem. Sci., (1981) 6:77). In order for a liposome to be an efficient gene transfer vector, one or more of the following characteristics should be present: (1) encapsulation of the gene of interest at high efficiency with retention of biological activity; (2) delivery of the aqueous contents of the vesicle to the target cell cytoplasm at high efficiency; and (3) accurate and effective expression of genetic information.

Liposomes are commercially available from Gibco BRL, for example, as LIPOFECTIN™ and LIPOFECTACE™, which are formed of cationic lipids such as N-[1-(2, 3 dioleyloxy)-propyl]-N, N, N-trimethylammonium chloride (DOTMA) and dimethyl dioctadecylammonium bromide (DDAB). Methods for making liposomes are well known in the art and have been described in many publications. Liposomes also have been reviewed by Gregoriadis, G. in Trends in Biotechnology, (1985) 3:235-241.

Compaction agents also can be used alone, or in combination with, a biological or chemical/physical vector of the invention. A "compaction agent", as used herein, refers to an agent, such as a histone, that neutralizes the negative charges on the nucleic acid and thereby permits compaction of the nucleic acid into a fine granule. Compaction of the nucleic acid facilitates the uptake of the nucleic acid by the target cell. The compaction agents can be used alone, i.e., to deliver the ica molecule in a form that is more efficiently taken up by the cell or, more preferably, in combination with one or more of the above-described vectors.

Other exemplary compositions that can be used to facilitate uptake by a target cell of the ica nucleic acids include calcium phosphate and other chemical mediators of intracellular transport, microinjection compositions, electroporation and homologous recombination compositions (e.g., for integrating a ica nucleic acid into a preselected location within the target cell chromosome).

The following examples are included for purposes of illustration and are not intended to limit the scope of the invention.

EXAMPLES

Example 1: Purification of dPNAG

It has been discovered according to the invention that dPNAG can be produced from any bacterial strain expressing the ica locus. Specifically, these include *Staphylococcus epidermidis, Staphylococcus aureus*, and other Staphylococcal strains such as *Staphylococcus carnosus* transformed with the genes in the ica locus. The following specific strains can be used according to the invention to purify PNAG from include *S. epidermidis* RP62A (ATCC Number 35984), *S. epidermidis* RP12 (ATCC Number 35983), *Staphylococcus epidermidis* M187, *S. carnosus* TM300 (pCN27), *S. aureus* RN4220 (pCN27), and *S. aureus* MN8 mucoid.

The following is a method that can be used for producing dPNAG from Staphylococci containing the ica locus.

Starting material is prepared from cultures of Staphylococci expressing the ica genes by growing the bacteria as follows: The polysaccharide is prepared from 16 liter cultures of bacterial growth medium. A preferred medium is a chemically-defined medium (CDM) based upon RPMI-1640 AUTO-MOD, a preparation of RPMI modified to allow sterilization by autoclaving (Sigma Chemical Co., St, Mo.). The CDM is supplemented with additional amino acids, vitamins and nucleotides to adjust their concentration to those found in other CDM (Hussain, M., J. G. M. Hastings, and P. J. White, 1991). A chemically defined medium for slime production by coagulase-negative Staphylococci. J. Med. Microbiol. 34:143-147. The medium is also supplemented with sucrose and glucose to a final concentration of 1%.

Liquid cultures are inoculated with a single colony of a polysaccharide-producing strain of bacteria. The preferred strain is designated *Staphylococcus aureus* MN8m, a strain that is a constitutive over-producer of the polysaccharide. A single colony is taken from a tryptic soy agar plate, or similar plate of bacterial growth medium, and grown at 37° C. Temperatures of 10-42° C. are also acceptable. Liquid cultures are incubated at 37° C. for 1-96 hours while being continuously stirred and flushed with oxygen at a rate of 2 liters/min. The pH is maintained at 7.0 throughout the growth period by the addition of 10 N NaOH via a pH titrator. At the end of the growth period, cell bodies are sedimented at 9000 g for 30 minutes and the supernatant concentrated to ~500 ml via tangential-flow filtration (10,000-500,000 molecular weight cutoff membranes). Two volumes of ethanol are added to precipitate the crude polysaccharide preparation. The precipitate is recovered by centrifugation, re-suspension in water and overnight dialysis against distilled water. The antigen is insoluble. The insoluble, crude antigen is suspended in 50 ml of phosphate buffered saline (PBS, 0.1 M phosphate, 0.15 M sodium chloride) to be digested with the lysozyme (0.5 mg) and lysostaphin (0.5 mg) for 0.5 to 16 h at 37° C. Antigen suspensions are further treated with nucleases (0.5 mg) at 37° C. for 0.5 to 16 h followed by incubation for 0.5 to 16 h with proteinase K (5 mg) at 37-56° C. After dialysis and lyophilization, dried extracts are dissolved in 5 M HCl and the pH adjusted to 2 with 4 N NaOH. Twenty ml aliquots of this solution are applied to a 5×88 cm column packed with SEPHACRYL S-300® (Pharmacia, Piscataway, N.J.) using 0.1 N HCl/0.15 M NaCl buffer with the eluted polysaccharide identified by optical absorption at 206 nm. Fractions corresponding to the polysaccharide representing a continuous range of molecular sizes are separately pooled, dialyzed against water, and lyophilized. Alternately, size fractionation can be performed with a variety of alternative procedures known in the art such as use of diafiltration membranes.

The level of acetylation can be adjusted by chemically-treating the native polysaccharide. Thus, polysaccharide with >50% acetate is isolated, and de-acetylated to achieve the desired acetylated level. Treatment is in a basic solution known to remove amino-linked acetate groups from glucosamine. A preferred means is incubation at 37° C. for 2-20 hours in 1.0 M NaOH. Weaker solutions and longer incubation times or higher temperatures, or stronger solutions with shorter incubation times or lower temperatures are equally effective. Generally, any treatment that raises the pH above 10 would be effective under the proper temperature.

There are also enzymatic means to de-acetylate the antigen. These include de-acetylating enzymes such as those related to chloroamphenicol de-acetylase and the icaB gene product.

Example 2: Preparation of dPNAG Diphtheria Toxoid (DTm) Conjugate Vaccine

DTm was covalently coupled to purified dPNAG by reductive amination. Aldehyde groups were first introduced onto the surface of diphtheria toxoid (DTm) by treatment of the protein with glutaraldehyde as described in step 1 below. Activated DTm was subsequently reacted with dPNAG, through its free amino groups in the presence of the reducing agent sodium cyanoborohydride as described in step 2 below.

Step 1: Activation of DTm with Glutaraldehyde 10 mg of DTm (4.86 mg/ml solution in 20 mM HEPES buffer, 50 mM NaCl, pH 8) were dialyzed against 0.1 M carbonate buffer (pH 10) for 3 hours (h) at room temperature using a 10 kDa MWCO dialysis cassette. When the protein solution was completely exchanged with carbonate buffer, glutaraldehyde was added to a final concentration of 1.25% and the mixture stirred at room temperature for 2 h. This produced activated DTm, which was exchanged with Phosphate Buffer Saline (PBS, pH 7.4) and concentrated to approximately 10 mg/ml by ultrafiltration using a 10 kDa MWCO filtration membrane.

Step 2: Coupling of Activated-DTm to PNAG

PNAG was purified as described in Maira et al. (Maira-Litrán T, Kropec A, Abeygunawardana C, Joyce J, Mark III G, Goldmann DA, and Pier GB. Immunochemical properties of the staphylococcal poly-N-acetyl glucosamine surface polysaccharide. Infect. Immun. 2002; 70:4433-4440). One fraction of this material, designated PNAG-II in Maira et al., was used to prepare the deacetylated PNAG (dPNAG). Native PNAG was dissolved to a concentration of 2 mg/ml in 5 M NaOH and incubated at 37° C. with stirring. After 18 h, the sample was placed in an ice slurry and allowed to cool to ≤10° C. 5 N HCl was also cooled on ice and added in 0.5 mL aliquots until the solution reached neutral pH. The dPNAG solution was then dialyzed overnight against distilled water in a 10 KiloDalton Molecular Weight Cutoff (10K MWCO) dialysis cassette and lyophilized. This procedure yielded dPNAG having 15-20% of acetate substitutions.

Purified dPNAG (10 mg) was dissolved in 0.25 ml of 5 M HCl, neutralized with an equal volume of 5 M NaOH and the final volume adjusted to 2 ml with PBS. dPNAG solutions are insoluble at neutral pH but remain completely soluble at slightly acidic or basic pH. Therefore to ensure solubility, the pH of dPNAG solutions was adjusted to 9.0. dPNAG (10 mg) was mixed with 1 ml of a 10 mg/ml solution of activated DTm in PBS and pH of the reaction adjusted to 7.5. Two hundred mg of purified sodium cyanoborohydride was added to the mixture and the reaction allowed to proceed in the dark for 14 h at 37° C. with mixing. After this time, the reaction mixture was exchanged by dialysis with 0.1 M carbonate buffer, 0.15 M NaCl, pH 10 (10 kDa MWCO dialysis cassette) and the high molecular weight conjugate was purified away from uncoupled components with a SUPEROSE 6® prep-grade column by gel filtration chromatography. dPNAG-DTm conjugate was dialyzed against 20 mM HEPES buffer, 50 mM NaCl, pH 8 and stored frozen at −2° C.

Example 3: Preparation of Native PNAG-DTm Conjugate Vaccine

Native PNAG (in this case, having 95%-100% acetate substitutions) was covalently coupled to purified DTm using the organic cyanylating agent 1-cyano-4-dimethylamino-pyridinium tetrafluoroborate (CDAP) to activate the polysaccharide hydroxyl groups as described in Step 1 below. CDAP-activated PNAG was subsequently coupled to DTm as described in Step 2 below without the need for additional spacer molecules.

Step 1: Activation of PNAG with CDAP 10 mg of purified PNAG were dissolved in 150 microliters of 5 M HCl, neutralized with an equal volume of 5 M NaOH and diluted up to 1 ml with borate buffer pH 9.2. CDAP was made up at 100 mg/ml concentration in acetonitrile and stored at −20° C. for up to 1 month. 200 microliters of CDAP (containing 20 mg) were slowly pipetted into a previously vortexed solution of PNAG-II (Maira, et al. Infect. Immun. 2002, 70: 4433-4440) in borate buffer (rapid addition of the organic co-solvent precipitates the polysaccharide) and the reaction was allowed to proceed for two minutes.

Step 2: Coupling of CDAP-Activated PNAG with DTm 5 mg of DTm (stock solution in 20 mM HEPES buffer, 50 mM NaCl, pH 8) were dialyzed against borate buffer pH 9.2 for 3 h with a 10 kDa MWCO dialysis cassette. After the activation of PNAG with CDAP, 5 mg of DTm was immediately added and the mixture reacted at room temperature for 3 h with stirring. After this time, the high molecular weight conjugate was purified from uncoupled components with a SUPEROSE 6® prep-grade column by gel filtration chromatography. Fractions containing PNAG-DTm conjugate were pooled, concentrated and stored frozen at −20° C.

Example 4: Production of Antiserum in Rabbits

Figure 2:
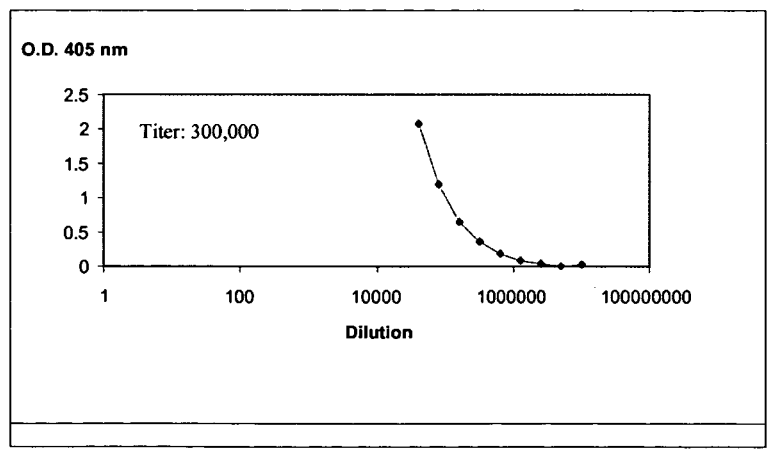
FIG. 2 shows binding of antibodies to deacetylated PNAG. The antibodies were raised to dPNAG conjugated to diphtheria toxoid.

Antibodies to purified PNAG-DTm or to dPNAG-DTm were raised in New Zealand white rabbits by subcutaneous immunization with two 10 µg doses of conjugated polysaccharide emulsified for the first dose in complete Freund's adjuvant and for the second dose in incomplete Freund's adjuvant, followed one week later by three intravenous injections of antigen in saline, each spaced three days apart. Rabbits were bled every two weeks and sera tested by ELISA. Binding curves obtained by ELISA from two representative rabbits immunized with either PNAG or dPNAG-DTm conjugates are shown in FIGS. 1 and 2, respectively. Titers were determined as described by Maira et al. (Maira-Litrán T, Kropec A, Abeygunawardana C, Joyce J, Mark III G, Goldmann DA, and Pier GB. Immunochemical properties of the staphylococcal poly-N-acetyl glucosamine surface polysaccharide. Infect. Immun. 2002; 70:4433-4440).

Example 5: Immunogenicity of PNAG-DTm and dPNAG-DTm in Mice

Figure 3:
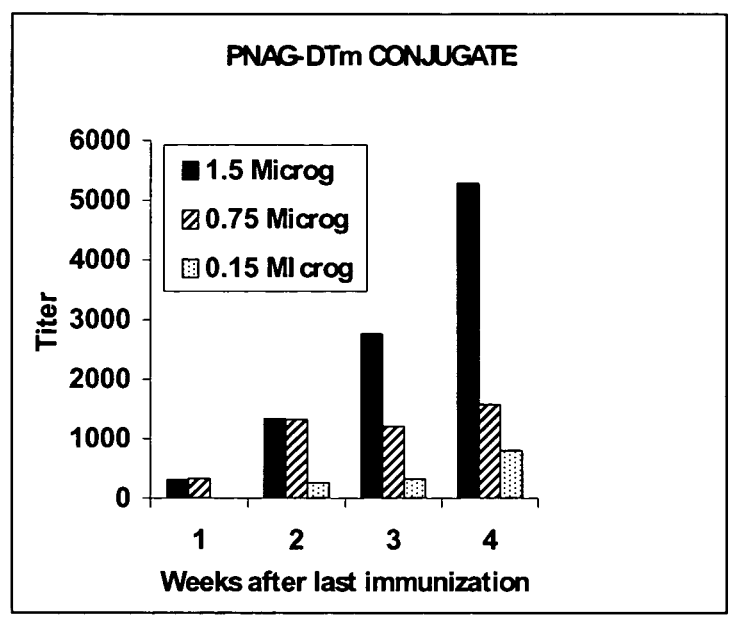
FIG. 3 shows antibody titers obtained in mice (10 per group) immunized 3 times subcutaneously, one week apart, with native PNAG coupled to diphtheria toxoid (DTm). Animals were immunized with the dose indicated in the legend. Blood samples were obtained at weekly intervals 1-4 weeks after the final immunization.
Figure 4:
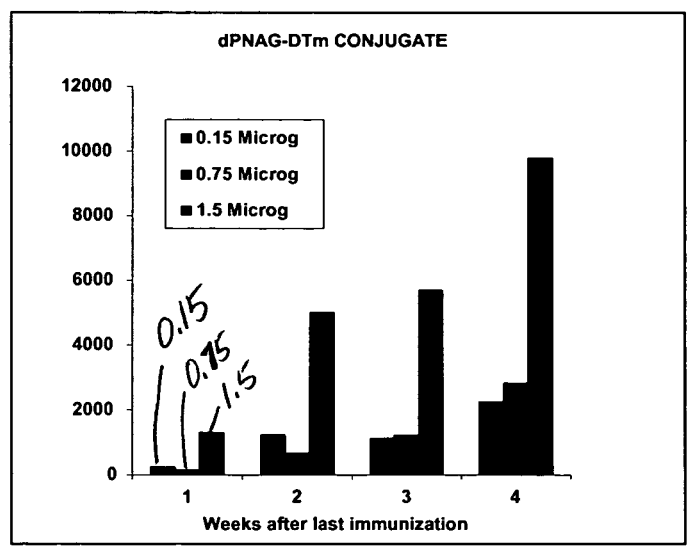
FIG. 4 shows antibody titers obtained in mice (10 per group) immunized 3 times subcutaneously, one week apart, with dPNAG coupled to diphtheria toxoid (DTm). Animals were immunized with the dose indicated in the legend. Blood samples were obtained at weekly intervals 1-4 weeks after the final immunization.
Figure 5:
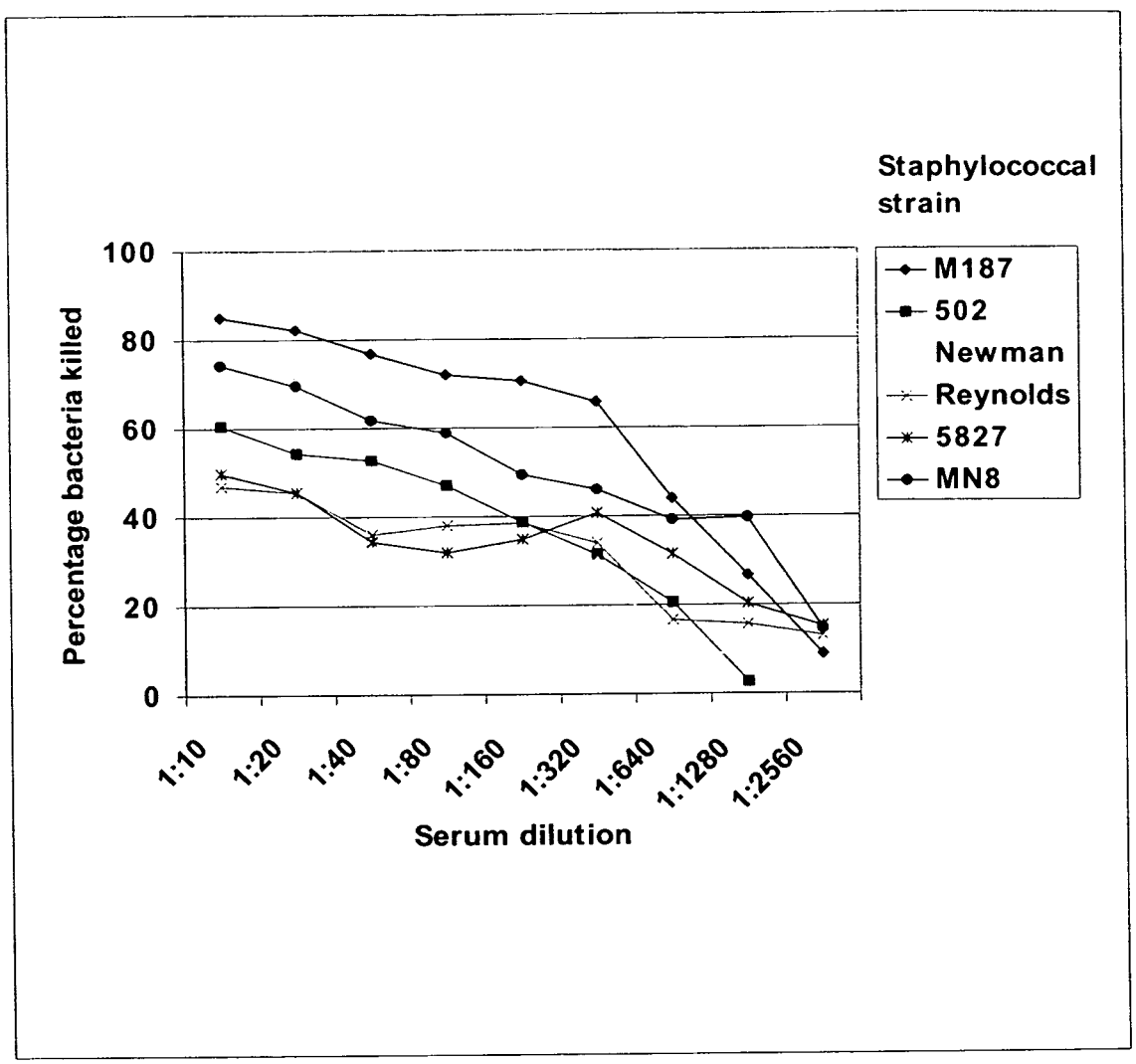
FIG. 5 shows opsonic killing of Staphylococcal strains as indicated in the legend by antibodies from sera of a rabbit immunized with dPNAG conjugated to diphtheria toxoid (rabbit 1). Each point shows mean percentage killed at the indicated dilution.
Figure 6:
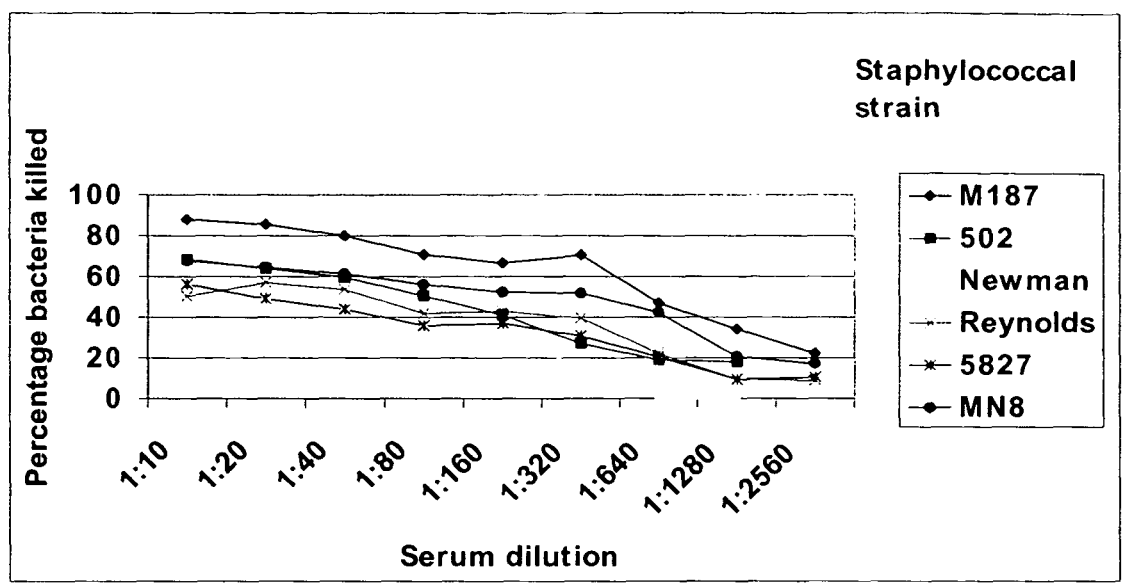
FIG. 6 shows opsonic killing of Staphylococcal strains as indicated in the legend by antibodies from sera of a rabbit immunized with dPNAG conjugated to diphtheria toxoid (rabbit 2). Each point shows mean percentage killed at the indicated dilution.
Figure 7:
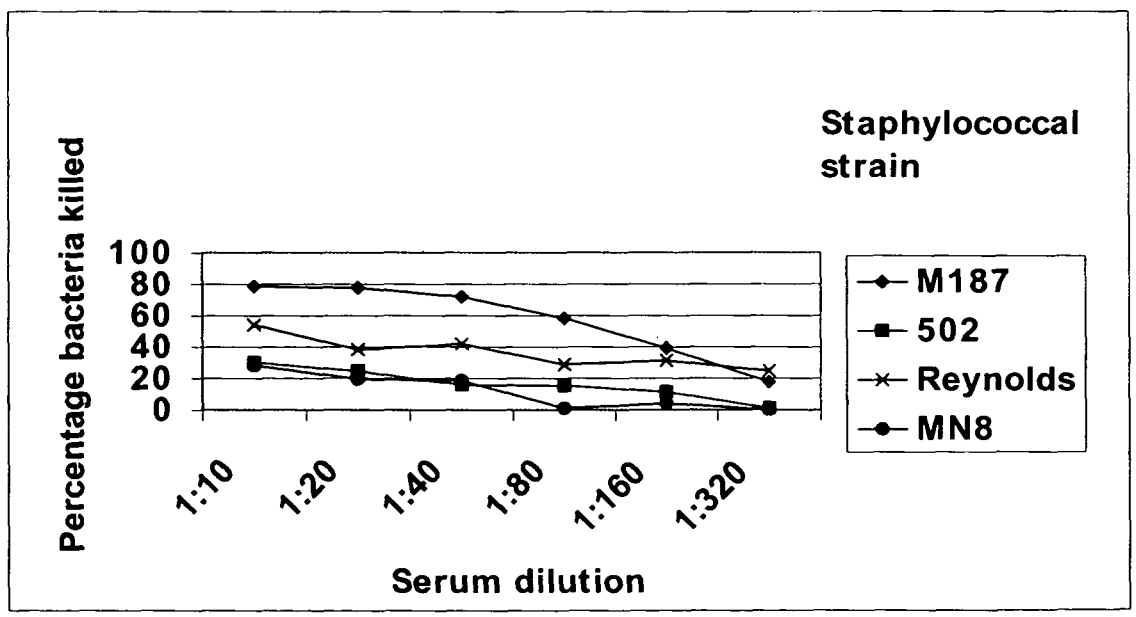
FIG. 7 shows opsonic killing of Staphylococcal strains as indicated in the legend by antibodies from sera of a rabbit immunized with native PNAG conjugated to diphtheria toxoid (rabbit 3). Each point shows mean percentage killed at the indicated dilution.
Figure 8:
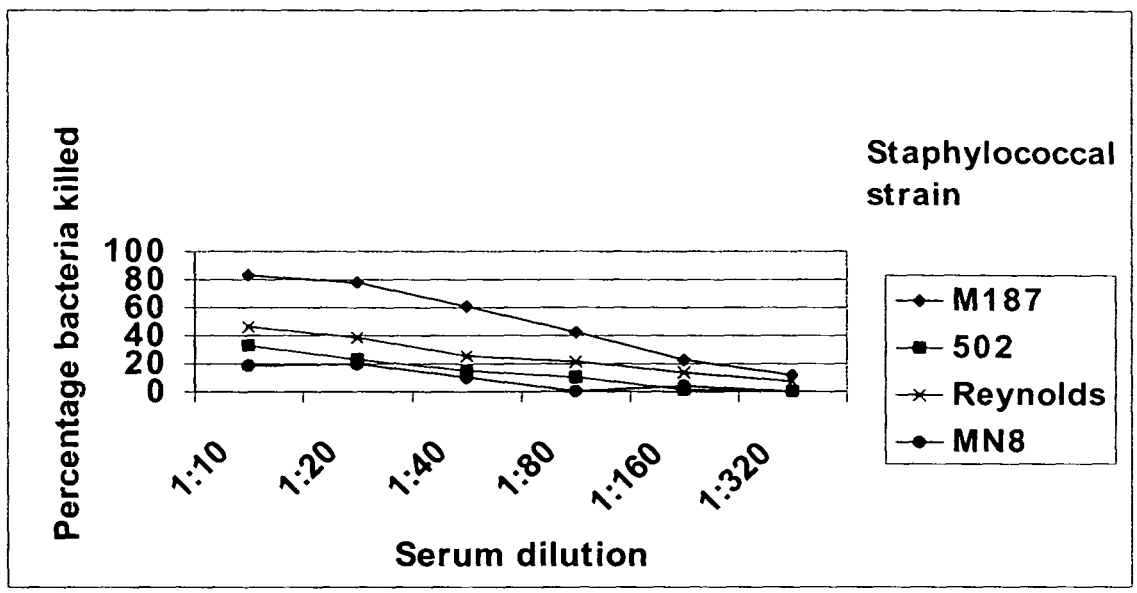
FIG. 8 shows opsonic killing of Staphylococcal strains as indicated in the legend by antibodies from sera of a rabbit immunized with native PNAG conjugated to diphtheria toxoid (rabbit 4). Each point shows mean percentage killed at the indicated dilution.

Groups of ten mice (Swiss Webster; female, 5-7 weeks of age) were immunized subcutaneously, one week apart, with 1.5, 0.75 or 0.15 µg of conjugated polysaccharide of PNAG-DTm and dPNAG-DTm in 0.1 ml of PBS and bled weekly for four weeks after the 3$^{rd}$ immunization. Control groups were immunized with a mixture of unconjugated polysaccharide and protein in the same ratio. Titers of mice immunized with the native and de-acetylated conjugates are shown in FIGS. 3 and 4, respectively. Control groups developed no titers at any on the doses used.

Figure 9:
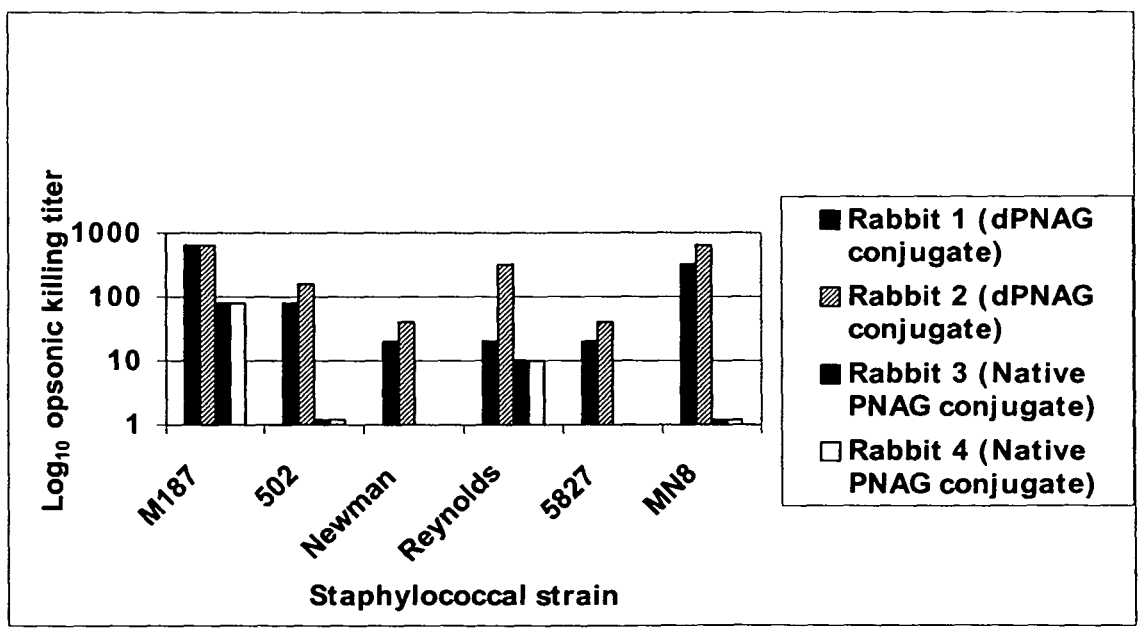
FIG. 9 summarizes the opsonic killing titers of antibodies from sera of the four rabbits against the Staphylococcal strains indicated on X-axis. The rabbits are as described in the Figure legends above. Each bar shows the reciprocal of the serum dilution at which ≥40% of the bacteria were killed. Bars <10 indicate sera unable to kill 40% of the bacteria at a 1:10 serum dilution.

Example 6: Opsonic Killing Activity of Rabbit Antisera Raised to PNAG and dPNAG Conjugated to Diphtheria Toxoid Two rabbits were immunized with PNAG conjugated to diphtheria toxoid and two rabbits were immunized with dPNAG conjugated to diphtheria toxoid as described above. Opsonic killing activity was determined using the method described by Maira et al. (Maira-Litrán T, Kropec A, Abeygunawardana C, Joyce J, Mark III G, Goldmann DA, and Pier GB. Immunochemical properties of the Staphylococcal poly-N-acetyl glucosamine surface polysaccharide. Infect. Immun. 2002; 70:4433-4440). The titer was determined, and defined as the serum dilution at which ≥40% of the bacteria were killed. Binding curves of the 4 rabbit antisera against a variety of Staphylococcal strains is shown in FIGS. 5-8. Strain M187 is a *S. epidermidis* strain; the others are all *S. aureus* strains. Titer comparisons are shown in FIG. 9.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, patents and patent publications that are recited in this application are incorporated in their entirety herein by reference.

We claim:

1. A composition comprising
an isolated β-1,6-glucosamine polymer conjugated to a protein or peptide carrier, wherein less than 40% of glucosamine amino groups in the isolated polymer are substituted with acetate, and
wherein the isolated polymer has the structure of

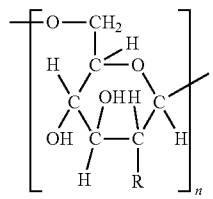

wherein n is an integer that is at least four, wherein R is selected from the group consisting of —NH—CO—CH₃ and —NH₂.

2. The composition of claim 1, wherein less than 35%, less than 30%, less than 25%, less than 20%, less than 15%, less than 10% or less than 5% of the glucosamine amino groups are substituted with acetate.

3. The composition of claim 1, wherein none of the glucosamine amino groups is substituted with acetate.

4. A composition comprising
an isolated β-1,6-glucosamine polymer, wherein less than 40% of glucosamine amino groups in the isolated polymer are substituted with acetate, wherein the composition is sterile, and
wherein the isolated polymer has the structure of

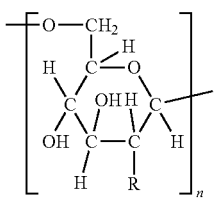

wherein n is an integer that is at least four, wherein R is selected from the group consisting of —NH—CO—CH₃ and —NH₂, and wherein the isolated polymer is conjugated to a carrier compound through a linker.

5. The composition of claim 1, wherein the peptide or protein carrier is tetanus toxoid.

6. The composition of claim 4, wherein the carrier compound is tetanus toxoid.

7. The composition of claim 1, wherein the composition is sterile.

8. A composition comprising
an isolated β-1,6-glucosamine polymer conjugated to a carrier compound through a linker, wherein less than 40% of glucosamine amino groups in the isolated polymer are substituted with acetate, and
wherein the isolated polymer conjugated to the carrier compound through a linker comprises the following structure:

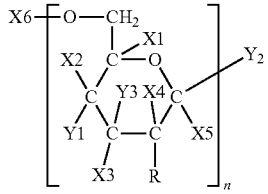

wherein each of X1, X2, X3, X4, X5 and X6 is either H or the linker, wherein each of Y1, Y2 and Y3 is either OH or the linker, provided only one of said X1, X2, X3, X4, X5, X6, Y1, Y2 or Y3 is the linker, wherein n is an integer that is at least four, and wherein R is selected from the group consisting of —NH—CO—CH₃ and —NH₂.

9. The composition of claim 8, wherein only one of said X1, X2, X3, X4, X5 or X6 is the linker.

10. The composition of claim 8, wherein only one of said Y1, Y2 or Y3 is the linker.

11. A composition comprising
an isolated β-1,6-glucosamine polymer conjugated to a carrier compound, wherein less than 40% of glucosamine amino groups in the isolated polymer are substituted with acetate, and
wherein the isolated polymer conjugated to the carrier compound comprises the following structure:

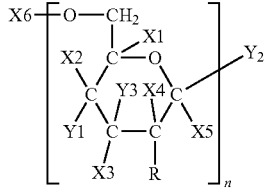

wherein each of X1, X2, X3, X4, X5 and X6 is either H, the carrier compound, or a linker joined to the carrier compound, wherein each of Y1, Y2 and Y3 is either OH, the carrier compound or a linker joined to the carrier compound, provided only one of said X1, X2, X3, X4, X5, X6, Y1, Y2 or Y3 is the carrier compound or the linker joined to the carrier compound, wherein n is an integer that is at least four, wherein R is selected from the group consisting of —NH—CO—CH$_3$ and —NH$_2$, wherein the carrier compound is a protein or a peptide.

12. An isolated polysaccharide conjugated to a carrier compound comprising
a β-1,6-glucosamine polymer, wherein less than 40% of glucosamine amino groups in the polymer are substituted with acetate, and
wherein the isolated polysaccharide conjugated to the carrier compound has the structure of

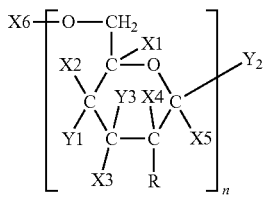

wherein each of X1, X2, X3, X4, X5 and X6 is either H, the carrier compound, or a linker joined to the carrier compound, wherein each of Y1, Y2 and Y3 is either OH, the carrier compound or a linker joined to the carrier compound, provided only one of said X1, X2, X3, X4, X5, X6, Y1, Y2 or Y3 is the carrier compound or the linker joined to the carrier compound, wherein n is an integer that is at least four, wherein R is selected from the group consisting of —NH—CO—CH$_3$ and —NH$_2$, wherein the carrier compound is a protein or peptide carrier.

13. The isolated polysaccharide conjugated to the carrier compound of claim 12, wherein the isolated polysaccharide conjugated to the carrier compound has the structure of

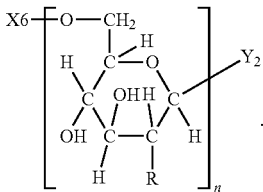

14. The isolated polysaccharide conjugated to the carrier compound of claim 12, wherein less than 35%, less than 30%, less than 25%, less than 20%, less than 15%, less than 10% or less than 5% of the glucosamine amino groups are substituted with acetate.

15. The isolated polysaccharide conjugated to the carrier compound of claim 12, wherein none of the glucosamine amino groups is substituted with acetate.

16. The isolated polysaccharide conjugated to the carrier compound of claim 13, wherein less than 35%, less than 30%, less than 25%, less than 20%, less than 15%, less than 10%, or less than 5% of the glucosamine amino groups are substituted with acetate.

17. The isolated polysaccharide conjugated to the carrier compound of claim 13, wherein none of the glucosamine amino groups is substituted with acetate.

18. The isolated polysaccharide conjugated to the carrier compound of claim 12, wherein the isolated polysaccharide has a molecular weight selected from the group consisting of at least 1000 Daltons, at least 1200 Daltons, at least 1500 Daltons, at least 2000 Daltons, at least 2500 Daltons, at least 5000 Daltons, at least 7500 Daltons, at least 10,000 Daltons, at least 25,000 Daltons, at least 50,000 Daltons, at least 75,000 Daltons, and at least 100,000 Daltons.

19. The isolated polysaccharide conjugated to the carrier compound of claim 12, wherein n is an integer that is in the range of 4-20.

20. The isolated polysaccharide conjugated to the carrier compound of claim 12, combined with a pharmaceutically acceptable carrier.

21. The isolated polysaccharide conjugated to the carrier compound of claim 12, wherein the isolated polysaccharide conjugated to the carrier compound is sterile.

22. The composition of claim 12, wherein the carrier compound is tetanus toxoid.

23. The composition of claim 1, further comprising a pharmaceutically acceptable carrier.

24. The composition of claim 1, wherein n is an integer that is in the range of 4-20.

25. The composition of claim 1, wherein the isolated polymer has a molecular weight of at least 2500 Daltons.

26. The composition of claim 1, wherein n is 5.

* * * * *

SEQUENCE LISTING

```
<160> NUMBER OF SEQ ID NOS: 1

<210> SEQ ID NO 1
<211> LENGTH: 6520
<212> TYPE: DNA
<213> ORGANISM: Staphylococcus aureus

<400> SEQUENCE: 1
ggtaccgagc tcgctaatag gtgactttgg ttgttcatgg acaattaaac ttgatgtact      60
tcttcgtgta ttcgtcatgg taattcctcg taaattaaaa tttttgtatt gaacctaaaa     120
taggtaatcc tagttgcgat tcaacatctt cttctgtctt aatacgctta tctaataatt     180
cttttaagaa aataatcaat attgctaaaa caataccaac aataatgctg ataactaagt     240
tgacagatac tattggagat acttttacgg cattatcatg tgctgaggaa agtatcgtaa     300
cattatcaac actcataatt ttaggcatgt catgagcaaa aactttagat attttattaa     360
caattttgtc agattcagat ttattcccag tggtaactga tacagtaata atttgagagt     420
ttgtttgatt ggttactttt aaaaatgaat tcaactcagc tgttgaatac tgaccatcaa     480
attctctaga tactttatct agaattctag gactttttgat aatttccgta tatgtattaa     540
cagactgcaa actactttga acattttgga aagctaaatc acttgaggac ttttttcatgt    600 tcactaatat ttgagtagaa gcagtatatt tgtcaggcat aacaaaaaag gttaatgccg     660
cacttactac aagacatatt gccggtaaaa taagcaataa tttaatattc ttctttagaa     720
tatttaatag ttttactaaa tcaaactttt ctttcatggt ttcctccaca taatcaatca     780
ttgtattcat tatgtatgtt ttataaatcg gacaattata tctagtttaa cgaccacaaa     840
acatacacaa ctacattttc tctaattatt tatataaata tttttatcgtt taaaattata    900 tcatgattct ctaccattat gtataactta tttatatttt tgcacaagat ataatattgt     960
ccaactttaa atatccaaac ctattaataa taaaactaga taccatcgta ctctgtcatg    1020
gctttcttat aatcgagtag aagcatcatc attacttgat tatttgctct ttacaacacc    1080
gagcgtgccc gtactcggta attcaatacc ttgcgtaacc cgtcactgtg agttgggtta    1140
atgataataa agcccacacc ttttaaaaag atgtgggtaa tttatataat ttttatttac    1200
atttttaact tataaaaaaa agcgcctatg tcatgattta ccatcacata ggcgcttatc    1260
aataaattat tacttattac tttccatttc atctaattta tgcggattcc ctgtaattag    1320
```

```
atgcaacttt attcttttca ggggaacatt acacttttat aatatgttca aagacaaact    1380
taaccattca caaatataaa gaataatatt atcaaatcat tgaacaaatc gtattttgca    1440
acaattgata tttatattaa tgtattgcat ttaatttata aaattcatat acatcttaat    1500
attctcaata tcgatttgta ttgtcaactt tatatagatt taaaaaaata atctcatgtc    1560
ttttttttaca aaagtaagtt aattattaca aactagtaac aaaaattatt tcttcaaaaa   1620
tatatttagt agcgaataca cttcatcttt gaattgactt ttactttctt ccactgctcc    1680
aaattttgc gaaaggatg ctttcaaata ccaactttca agaaacagca atattaaatt       1740
ctgaaagtct tcttttgtca tctttatctt tgattcatca tagaattttg ctatctcttt    1800
acttaatgat tgatttaaat cttgtatttg tccgtaaata tttccagaaa attcctcagg    1860
cgtattagat aattgaacgt acattctaat ataccttct tcgatgtcga aaataaactc     1920
aaataagaat tgatataaag catcaattga atagttcgat ttattttgat tcatcataat    1980
aatattatta aggtaatcaa acaacatttt aacactttgt tcgtaaatac ttttttttcga   2040
gtcaaaatgg taatataaac tcgctttctt tatatttaca ctttagcta tatcatcaag     2100
tgttgtaccg tcataccct tctctgaaaa taaggttatt gcgttatcaa taatcttatc     2160
cttcaatttt tataaccccc tactgaaat taatcacact atgttacagg aaaattaagt     2220
tgcaattaca aatatttccg tttaattata acaacaatct attgcaaatt aaaatactat    2280
caattaccat atggcttaca acctaactaa cgaaaggtag gtaaagaaat tgcaattttt    2340
taacttttg cttttttatc ctgtatttat gtctatttac tggattgtcg gttcaattta     2400
tttctatttc accagagaaa ttagatattc attgaacaag aagcctgaca taaatgtgga    2460
tgaattagaa ggcattacat ttttacttgc ctgttataac gaaagtgaaa cgattgaaga    2520
tacgttgtct aatgttcttg cactcaaata cgagaagaaa gaattatta tcattaatga    2580
tggaagttca gataatacag cagaactcat ctataaaatc aaagaaaata atgactttat    2640
tttcgtcgat ttacaagaaa acagaggtaa agccaacgca ctcaatcaag gcattaaaca    2700
ggcttcatat gattatgtaa tgtgcttgga tgcagatact atcgttgatc aagatgcacc    2760
atattatatg attgagaatt tcaaacatga tccaaaactt ggtgcggtta caggtaatcc    2820
tagaattcga aataagagtt ctattttagg taaaattcaa acgatagaat atgcaagttt    2880
aattggctgt attaagcgaa gtcagacact tgctggcgca gtcaatacta tttcgggtgt    2940
cttcactcta tttaaaaaaa gtgcagttgt cgacgttggc tactgggata ctgatatgat    3000
taccgaagat attgcagttt cttggaaatt gcatttacgt ggatatcgta ttaagtatga    3060
accgcttgcc atgtgttgga tgttggttcc agaaacattg ggaggtcttt ggaagcaacg    3120
cgtgagatgg gctcaagggg gacacgaagt attactacga acttttttta gcacaatgaa    3180
aacgaaaagg tttcctttat atattttgat gtttgagcaa atcatctcga ttttatgggt    3240
atatatagtg cttctatatt taggctattt gttcataaca gcaaacttct tagactatac    3300
atttatgaca tatagttttt caatatttct actatcatca tttactatga ctttataaa    3360
cgttattcaa tttacagtcg cactctttat tgatagtcgc tacgagaaaa agaatatggc    3420
tggactcata tttgtaagtt ggtatccgac agtatactgg attattaacg cagcagtagt    3480
tcttgtcgca tttccaaaag cattaaaacg taagagaggt ggttacgcaa catggtcaag    3540
cccagacaga gggaataccc aacgctaaaa tcatcgctaa atattgtaag agaaacagca    3600
cttatcgcta tatcttgtgt cttttggata tattgtttag ttgttctact cgtttatatt    3660
ggtactatat ttgaaattca tgacgaaagt atcaatacaa tacgtgttgc tttaaacatt    3720
```

```
gaaaatactg aaattttaga tatatttgaa actatgggca ttttcgcgat tatcattttt    3780
gtattttta  caattagcat attgattcaa aaatggcaga gagggagaga atcgtgaagt    3840
atagaaaatt tataatttta gtgttgagta tcttgatcat attgcctgta agcacactgg    3900
atggtcatca tattgcaaat gcagatgacg attcacctaa aaaactgaaa tataaagaaa    3960
atagtgctct ggcattaaat tatcaccgtg taagaaaagc gaattttctg aataatttta    4020
tttacttctt ttctagtagt aaagaaatta aaaattatag tgttagtcaa tcacaatttg    4080
aatctcaaat aaaatggcta aaatcacatg atgctaaatt tttaaccttg aaagaatttt    4140
tatattacaa gaaaaaaggt aagttccaa  acgaagtga gtgggttaac tttgatgata    4200
tggatgaaac tatttatgaa aatgcttatc caatcttaaa aaaatataaa ataccggcga    4260
ctgggtttat tatcacaggt catgttgggg gggaaaactt tcacaacctc gatatgatta    4320
gtaaaaaaga actaaagaa  atgtataaaa ctgggttatg ggaatttgaa acacataccc    4380
acgatttgca taacttatct aaaaataata agtcaaaatt aatgaaagct tctgaagcta    4440
caatcataaa agatttaaac aaaagtgaaa aatatctaac taaaaacttt aaaaagtcgc    4500
agaaaactat agcctatcct tatggcttga tgaatgacga taaattaccg gtaatcaaaa    4560
aagctgggtt aaaatacggt ttttcattag aggaaaaagc agtcactccg aactccaatg    4620
attattacat ccctagaata ttaattagtg atgatgcttt tgagcattta attaagagat    4680
gggacggatt ccatgaaaaa gattagactt gaactcgtat atttacgtgc tattatatgt    4740
gcaattatta ttatcacaca tttacttaca caaattactt taaaacatga aaatatggag    4800
ggtgggtcct tagtgttaca attttacatt cgtaatattg tgattttttgg tacaccttgc    4860
tttattatct tgtcacagtt actgacaacc ttgaattacc aaaaagtcac ctatagatac    4920
ttaactacac gcgtaaaata tatacttatt ccttacatat taatgggatt gttttacagt    4980
tatagtgaat cattattaac agattcaagt ttcaataaac aattcattga aaatgtccta    5040
ttaggtcaat ggtatggcta ttttatcgtt gttatcatgc aattctttat tttgagttat    5100
atcattttta aaattaacta taacctattc aacagtaaaa tattattatt gttatcttt     5160
attttacagc aatcattttt atattacttt acgaacaaca cagcgtttca cgataccgtg    5220
ctacactatt atcccttaag tgaaaatact ataatattcg gatggatttt ttatttcttc    5280
ttaggtgcat atatgggtta taactacgaa cgtgtattaa atttcttaga acgttattta    5340
gttattatga ttgtattagc tgtagctact tattttgtgt ttattgcgtt agcaaatgga    5400
gactattgga acgttaccag cttttcatat tcattaacac catataatag tattatgttt    5460
attgttatct tgggtatttg cacgcatttt aaaacaatgt tatttaatac gattcaaatg    5520
attagtgctt tctcattctt tatttattta ttacatccaa tcattctaga ctcattgttt    5580
gcatatacaa atatatttga ggataataca atggtctttc tagcgatatc actactattc    5640
attttaggat tatgtatagg tgtcggcatg atattgcgtg aattctatat ctttaggttt    5700
attattggaa acaaccata  taaattgaac attaatgctt attaattatt aagctatgtt    5760
aaaaacacgc ggtgggcgaa atcagtttga attgactgac ttcgttttac cgcgtgttta    5820
atattgttat acatatattc taattgcaca tttaaacttc gtaaatgcca atgggagtgg    5880
gacagaaatg atattttcgc aaaatttatt tcgtcgtccc acccccaactt gcacattatt    5940
gtaacctgac tttccgccag cttctatgtt ggggccccgc caacttgcac attattgtaa    6000
gctgactttc cgccagcttc tttgttgggg cccgccaac  ttgcattgtt tgtagaattt    6060
```

| | | | | | |
|---|---|---|---|---|---|
| cttttcgaaa | ttctttatgt | tggggcctcg | cccaatgttt | tacttgaata | attcttttag 6120 |
| aattctaaat | aatgatccga | ttaattgaaa | gaagtctgca | gtcattatta | attcctccct 6180 |
| ttactttata | aattatgctt | gcttagtatc | agtcagcttt | tcagttttca | ctaaatcgtc 6240 |
| tgctaaatga | tgccaaaaat | cttgtaattc | ttctcttgtg | cgcactgtat | cagaactgtc 6300 |
| ttgtcctaca | aagtcaacat | gatcccaatc | atgttttgta | ggcgtcactt | gccaaatgcc 6360 |
| tttttgaatt | ttatctgtcg | cttttgtata | agcttgatta | aatggatgtt | gagaagaaat 6420 |
| aacggatact | aaaccatcgt | tttctcgcca | ttcttttttca | gtagctttac | cgattaagtt 6480 |
| accagtaatc | acaaatggga | aaaacatatt | taagtctgct | | 6520 |